(12) United States Patent
Abe

(10) Patent No.: US 10,531,861 B2
(45) Date of Patent: Jan. 14, 2020

(54) ULTRASONIC DIAGNOSIS APPARATUS

(71) Applicant: Toshiba Medical Systems Corporation, Otawara-shi (JP)

(72) Inventor: Yasuhiko Abe, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 687 days.

(21) Appl. No.: 14/663,108

(22) Filed: Mar. 19, 2015

(65) Prior Publication Data

US 2015/0223781 A1 Aug. 13, 2015

Related U.S. Application Data

(63) Continuation of application No. PCT/JP2013/077177, filed on Oct. 4, 2013.

(30) Foreign Application Priority Data

Oct. 4, 2012 (JP) ................................. 2012-222590

(51) Int. Cl.
*A61B 8/08* (2006.01)
*A61B 8/12* (2006.01)
*A61B 8/06* (2006.01)

(52) U.S. Cl.
CPC .............. *A61B 8/488* (2013.01); *A61B 8/065* (2013.01); *A61B 8/0883* (2013.01); *A61B 8/12* (2013.01)

(58) Field of Classification Search
CPC .................................................... A61B 8/488
See application file for complete search history.

(56) References Cited

U.S. PATENT DOCUMENTS 5,148,808 A * 9/1992 Satake ..................... A61B 8/06
600/441
5,249,577 A * 10/1993 Shinomura .............. A61B 8/06
600/441

(Continued)

FOREIGN PATENT DOCUMENTS

CN 20980680 Y 11/2007
CN 101094611 A 12/2007

(Continued)

OTHER PUBLICATIONS

Office Action dated Mar. 24, 2016 in Chinese Patent Application No. 201380052105.5 (with English translation of category of cited documents).

(Continued)

*Primary Examiner* — Rochelle D Turchen
(74) *Attorney, Agent, or Firm* — Oblon, McClelland, Maier & Neustadt, L.L.P.

(57) ABSTRACT

An ultrasound diagnosis apparatus includes an ultrasound transceiver and a controller. The ultrasound transceiver includes a changer that changes transmission direction of ultrasound waves. The ultrasound transceiver transmits ultrasound waves in a direction set while being inserted in a subject to acquire biological information of an observation site of the subject. The controller obtains a direction toward the observation site based on the biological information, and controls the changer to adjust the transmission direction of ultrasound waves to the direction thus obtained.

18 Claims, 28 Drawing Sheets

(56) References Cited

U.S. PATENT DOCUMENTS

| | | | |
|---|---|---|---|
| 6,645,147 B1 * | 11/2003 | Jackson | A61B 8/06 600/458 |
| 8,923,949 B2 | 12/2014 | Amit | |
| 2007/0016050 A1 * | 1/2007 | Moehring | A61B 8/06 600/454 |
| 2007/0016072 A1 * | 1/2007 | Grunwald | A61B 5/06 600/468 |
| 2008/0081993 A1 | 4/2008 | Waki | |
| 2008/0097217 A1 * | 4/2008 | Itoh | A61B 5/6848 600/459 |
| 2009/0048489 A1 | 2/2009 | Igarashi et al. | |
| 2009/0069684 A1 * | 3/2009 | Shibata | A61B 8/0833 600/443 |
| 2009/0149759 A1 | 6/2009 | Baba et al. | |
| 2010/0249597 A1 * | 9/2010 | Shi | A61B 8/06 600/454 |
| 2010/0312109 A1 | 12/2010 | Satoh | |
| 2013/0308850 A1 * | 11/2013 | Oikawa | G01S 7/52085 382/131 |
| 2013/0331702 A1 * | 12/2013 | Yan | A61B 5/022 600/454 |

FOREIGN PATENT DOCUMENTS

| | | |
|---|---|---|
| CN | 101268953 A | 9/2008 |
| CN | 10144998 A | 6/2009 |
| JP | 05-161649 A | 6/1993 |
| JP | 2002-306485 A | 10/2002 |
| JP | 2006-150053 A | 6/2006 |
| JP | 2010-279506 A | 12/2010 |
| JP | 2012-081362 A | 4/2012 |

OTHER PUBLICATIONS

International Search Report dated Nov. 12, 2013 for PCT/JP2013/077177 filed Oct. 4, 2013 with English Translation.

* cited by examiner

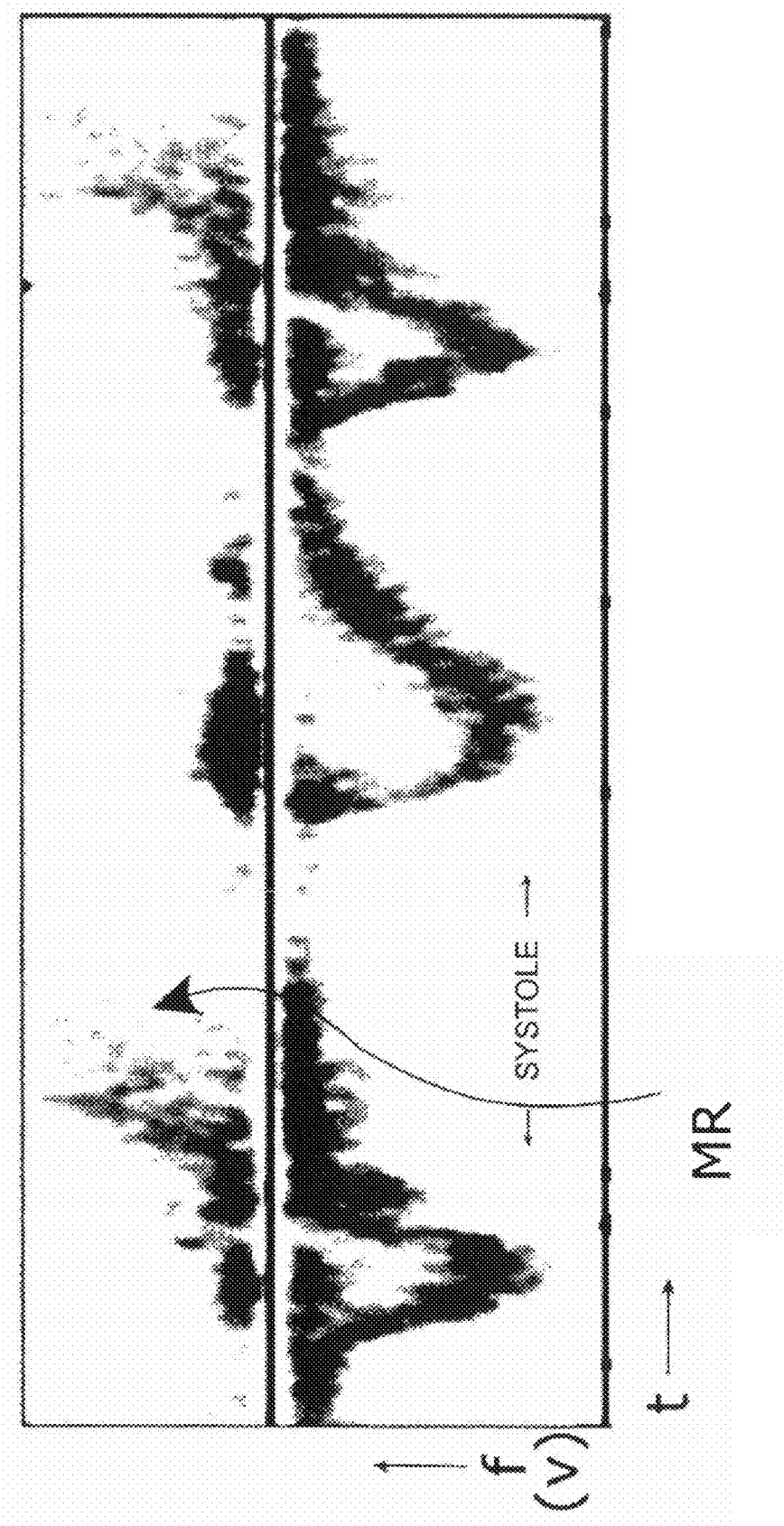

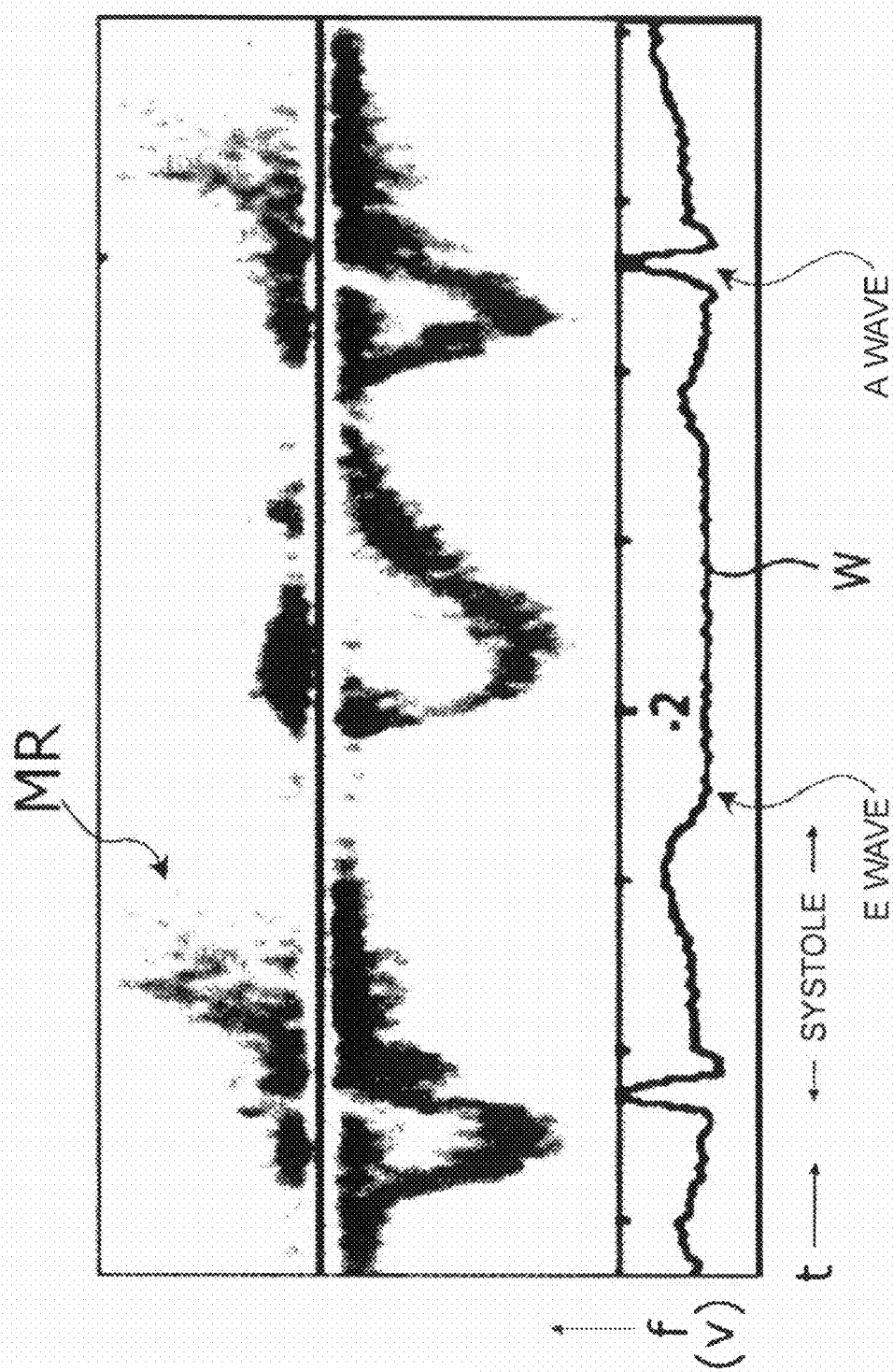

ULTRASONIC DIAGNOSIS APPARATUS

CROSS-REFERENCE TO RELATED APPLICATION

This application is based upon and claims the benefit of priority from Japanese Patent Application No. 2012-222590, filed Oct. 4, 2012; the entire contents of which are incorporated herein by reference.

FIELD

Embodiments described herein relate generally to an ultrasound diagnosis apparatus.

BACKGROUND

A medical image diagnosis apparatus is a device that creates, for examination and diagnosis, medical images (B-mode image, blood flow image, etc.) from information on tissues in a subject without surgical removal of the tissues. Examples of such medical image diagnosis apparatus include X-ray diagnosis apparatuses, X-ray CT (Computed Tomography) apparatuses, MRI (Magnetic Resonance Imaging) apparatuses, and ultrasound diagnosis apparatuses.

In one example, after the image of a subject is captured, the medical image is stored in a medical image system (e.g., PACS; Picture Archiving and Communication Systems) in a healthcare institution. After that, a radiologist or the like retrieves the medical image from the medical image archive system to interpret it. In another example, after the image of a subject is captured, the medical image is displayed immediately (in real time) for inspection by a doctor or the like. In this manner, medical images may be used so that a doctor or the like can promptly know about conditions inside the subject's body. In still another example, medical images may be used to monitor conditions inside the subject's body during a specific period for a follow-up. An ultrasound diagnosis apparatus may be used in this monitoring. In this case, the ultrasound diagnosis apparatus is used in consideration of such a point as that it does not cause radiation exposure to the subject.

In one example of examination and diagnosis, when conditions inside the subject's body are monitored for a certain period, it may be difficult to keep the subject in a gantry (an X-ray CT apparatus, an MRI apparatus, etc.) depending on the length of the period. The same is applied to X-ray diagnosis apparatuses that require the subject to be kept between an X-ray irradiator and a detector. In contrast, the ultrasound diagnosis apparatus does not need a gantry or the like. The ultrasound diagnosis apparatus transmits/receives ultrasound waves to/from an observation site with an ultrasound probe or the like, thereby obtaining information on body tissues to be imaged. In addition, the ultrasound diagnosis apparatus does not make noise due to vibration of a gradient magnetic field coil unlike MRI apparatuses.

However, if the ultrasound probe transmits/receives ultrasound waves to/from the observation site from outside the body, there may be the influence of tissues (bones, lungs, etc.) present in the way to the desired observation site from the outside. To solve the problem, the ultrasound diagnosis apparatus is provided with a transesophageal echocardiography (TEE) probe. The ultrasound diagnosis apparatus having the TEE probe transmits/receives ultrasound waves to/from the observation site from the esophagus or the upper digestive tract. This enables the ultrasound diagnosis apparatus having the TEE probe to obtain the ultrasound image of a desired observation site without the influence of the tissues (bones, lungs, etc.) as mentioned above.

As a structure example, the TEE probe includes a guiding hollow tube part, an end part, and a curved part. The guiding hollow tube part has a predetermined length. The end part has an ultrasound transducer. The curved part connects the guiding hollow tube part with the end part. The portion from the guiding hollow tube part to the end part is inserted in the body cavity, for example, in the upper gastrointestinal tract, such as the esophagus and the stomach. Therefore, the guiding hollow tube part is formed to be flexible. The end of the guiding hollow tube part opposite to the end part is connected to a gripper. The gripper is held by the operator. The gripper is provided with an operation unit. The operation unit is used to manipulate the curved part and the end part. A wire is strung from the gripper through the guiding hollow tube part to the end part. The wire is used to bend the curved part.

By the operation on a scanner provided to the gripper, the wire is driven. In response to the driving of the wire, the curved part is bent. When the curved part is bent, the end part is pointed in a predetermined direction. While the end part is pointed in the predetermined direction, the TEE probe transmits/receives ultrasound waves to/from a desired observation site by the ultrasound transducer of the end part. With this, the ultrasound diagnosis apparatus having the TEE probe can obtain an image that indicates, for example, conditions of the heart from a predetermined location in the esophagus.

In the body cavity, due to the influence of pulsating and breathing, there may be a change in the relative positions of the end part of the TEE probe and the desired observation site. When the observation site is monitored for a predetermined period as described above, it can be a burden for the operator of the ultrasound diagnosis apparatus to keep monitoring the shift of the end part all the time and adjust the position if necessary, resulting in a reduction in the efficiency of the examination.

BRIEF DESCRIPTION OF THE DRAWINGS

FIG. 7A is a schematic diagram of an example of a Doppler spectrum image generated by the generating unit of the first embodiment;

FIG. 7B is a schematic diagram of an example of ECG (electrocardiogram) waveform and the Doppler spectrum image generated by the generating unit of the first embodiment;

DETAILED DESCRIPTION

In general, according to one embodiment, an ultrasound diagnosis apparatus includes an ultrasound transceiver and a controller. The ultrasound transceiver includes a changer that changes transmission direction of ultrasound waves. The ultrasound transceiver transmits ultrasound waves in a direction set while being inserted in a subject to acquire biological information of an observation site of the subject. The controller obtains a direction toward the observation site based on the biological information, and controls the changer to adjust the transmission direction of ultrasound waves to the direction thus obtained.

Referring to FIGS. 1 to 20B, a description is given of an ultrasound diagnosis apparatus according to first to seventh embodiments.

[First Embodiment]

Figure 1:
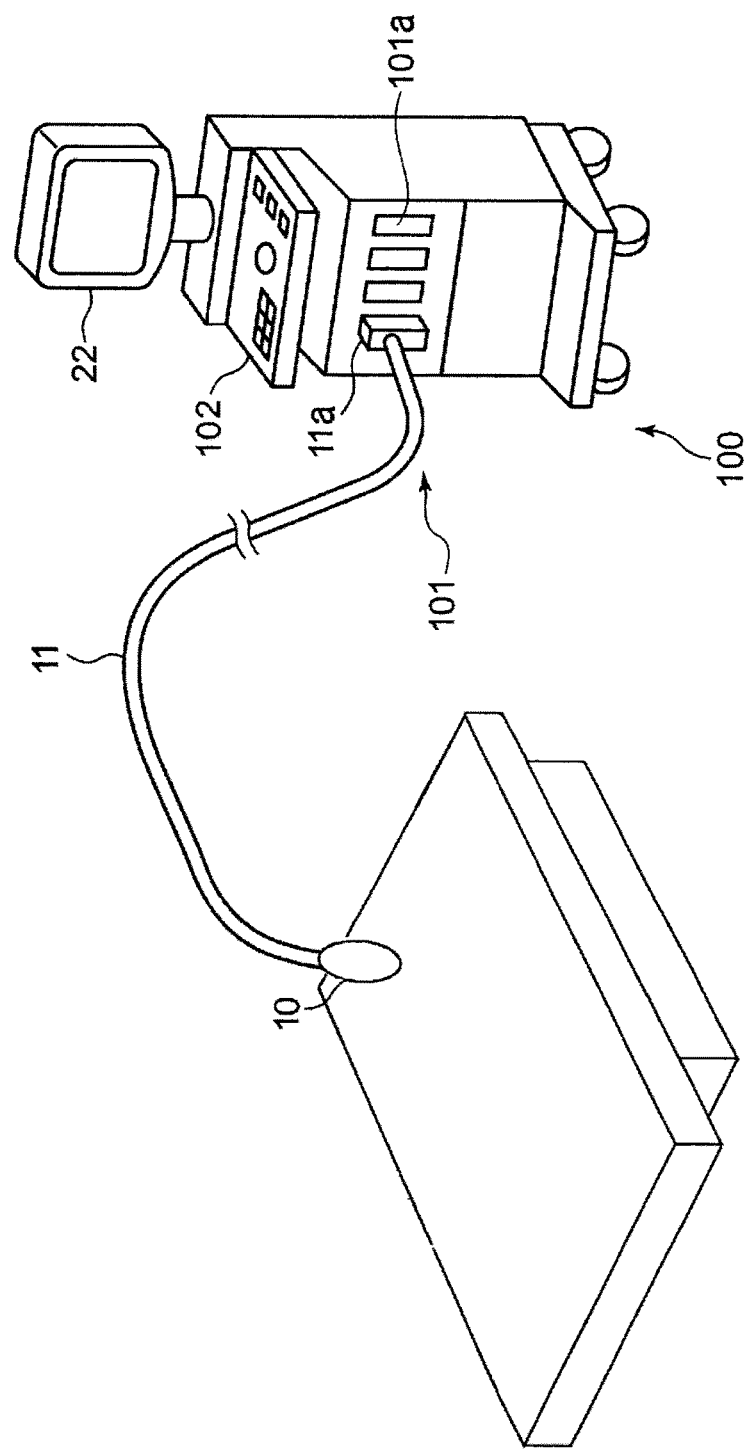
FIG. 1 is a schematic perspective view of an ultrasound diagnosis apparatus.

The overview of the overall structure of the ultrasound diagnosis apparatus 100 according to the first embodiment is described first with reference to FIG. 1. FIG. 1 is an external view of the ultrasound diagnosis apparatus 100 for explaining the overview of its structure.

As illustrated in FIG. 1, the ultrasound diagnosis apparatus 100 of the embodiment includes a main body 101 and an end part 10. The end part 10 and the main body 101 are connected through a cable 11. In the example of FIG. 1, a connector 11a is provided to the end of the cable 11. The main body 101 is provided with connection parts 101a. The connection parts 101a are formed to be connectable to the connector 11a. The main body 101 includes an operation unit 102 and a display unit 103. The operation unit 102 is used to operate the ultrasound diagnosis apparatus 100. The display unit 103 displays an image generated by the ultrasound diagnosis apparatus 100 and other images. Incidentally, the illustration of the ultrasound diagnosis apparatus 100 in FIG. 1 is by way of example only. The structure of the main body 101, the arrangement and the structure of the cable 11, the operation unit 102 and the display unit 103, and the like are not limited to those in FIG. 1, and susceptible to various modifications as appropriate. For example, instead of being configured as illustrated in FIG. 1, the main body 101 may be configured as a portable ultrasound diagnosis apparatus.

<Structure of End Part>

Figure 2A:
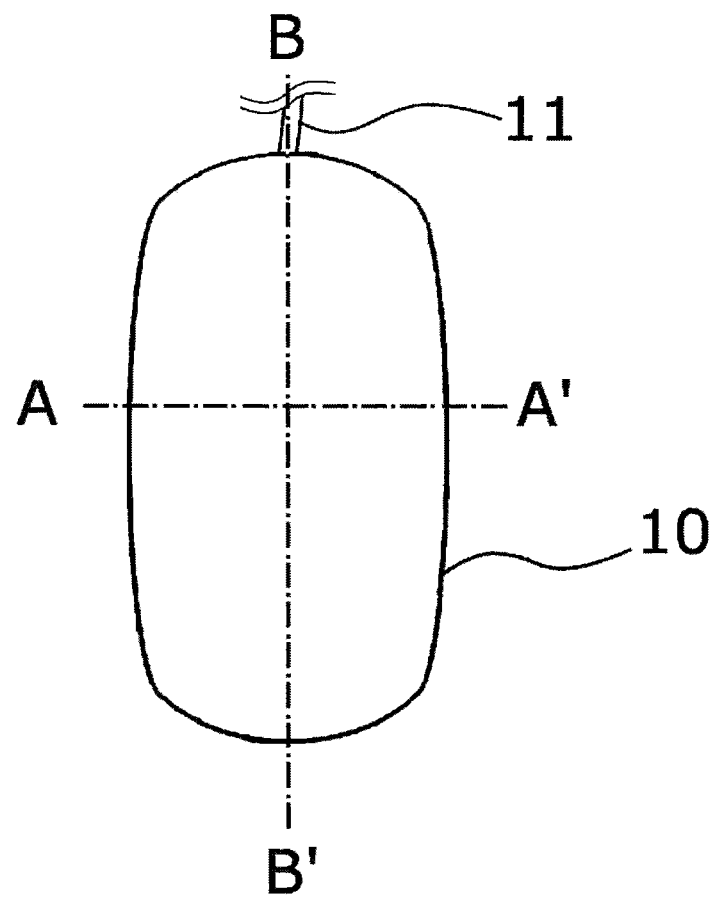
FIG. 2A is a schematic side view of an end part.
Figure 2B:
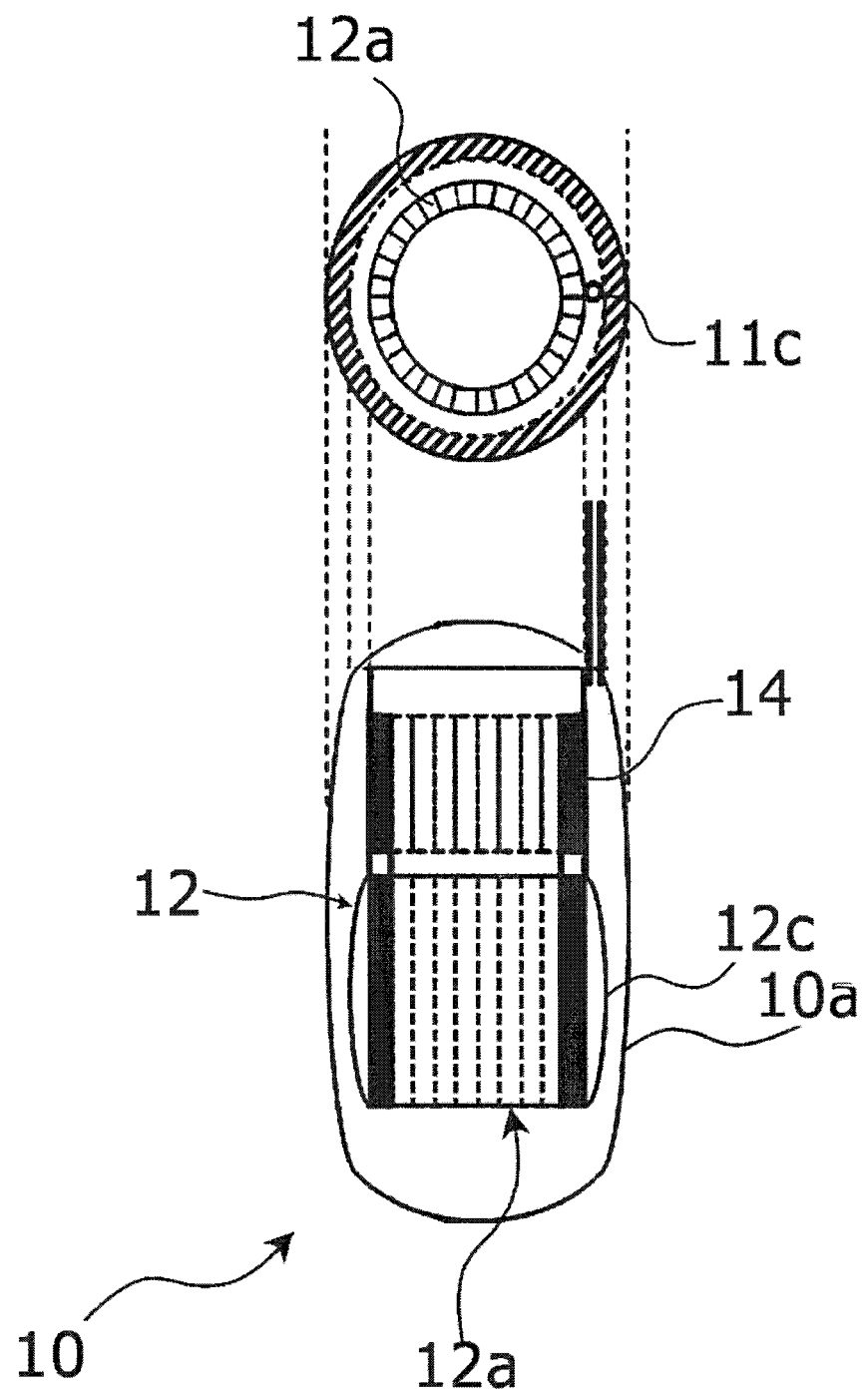
FIG. 2B provides schematic cross sections taken along lines A-A' and B-B' in FIG. 2A, illustrating the positional relationship of parts therein.
Figure 3A:
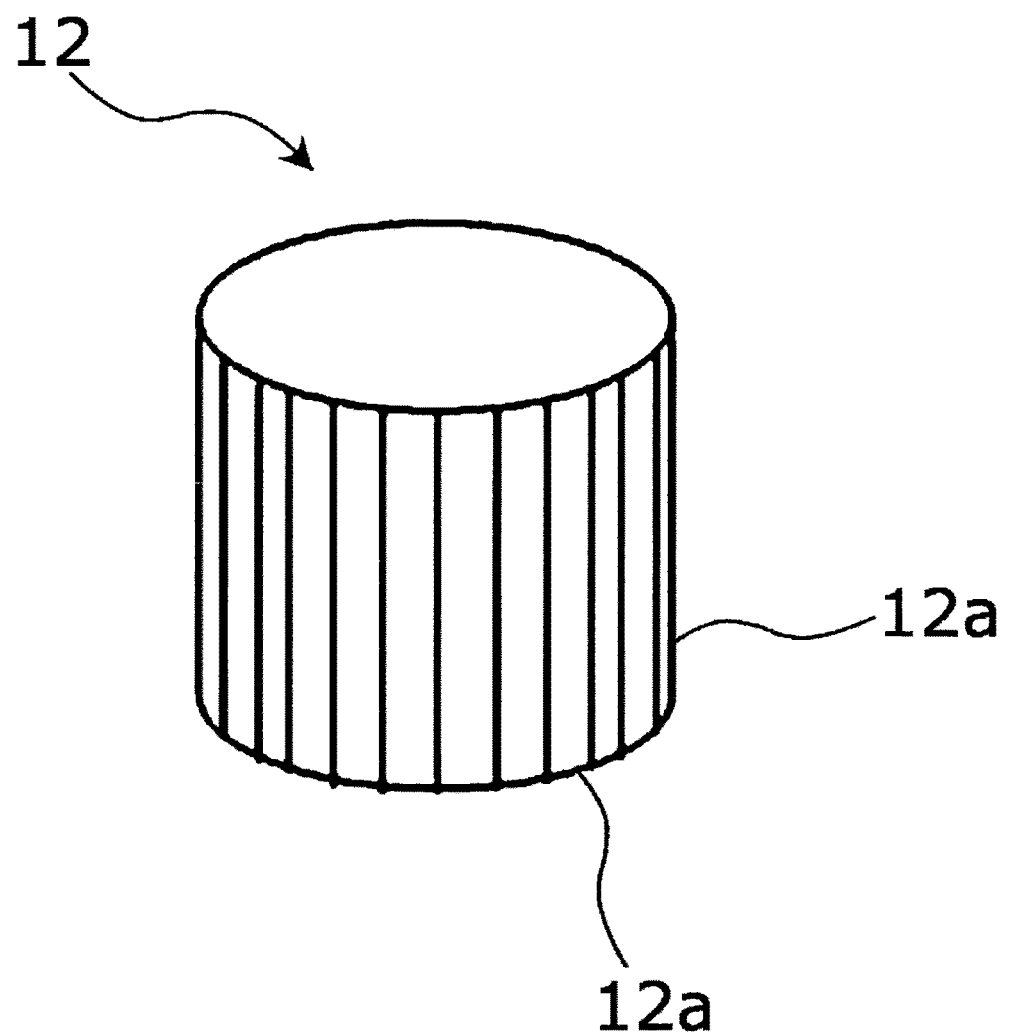
FIG. 3A is a schematic perspective view of the ultrasound transducer.

In the following, the structure of the end part 10 is described with reference to FIGS. 2A, 2B, and 3A. FIG. 2A is a schematic side view of the end part 10. FIG. 2B provides schematic cross sections taken along lines A-A' and B-B' in FIG. 2A, and illustrates the positional relationship of parts therein. In FIG. 2B, the cable 11, a direction controller 16, and a drive unit 18 are not illustrated. FIG. 3A is a schematic perspective view of an ultrasound transducer 12, which is a one-dimensional (1D) transducer array where ultrasound oscillators 12a are provided all over the outer peripheral surface of a support.

(Overview of End Part)

In the examples of FIGS. 1 and 2A, the end part 10 in a capsule form is used as a device for transmitting/receiving ultrasound waves. As illustrated in FIG. 2B, the end part 10 includes a container 10a. The container 10a is formed in an ellipsoid. The container 10a includes therein the ultrasound transducer 12, a transmit-receive controller 14, and an interface (I/F) 15 (see FIG. 4). The direction controller 16 and the drive unit 18 may be provided inside the container 10a. FIG. 2B does not illustrate the direction controller 16 and the drive unit 18 of this case.

As illustrated in FIG. 2B, in the ellipsoidally formed end part 10, for example, the cable 11 is connected to one longitudinal end of the container 10a. A power supply line and a signal line in the cable 11 run through the inside of the container 10a. These lines are connected to the transmit-receive controller 14, the direction controller 16, and the drive unit 18. When the container 10a is configured to be placed on tissue in the subject's body, the cable 11 can be configured to prevent the end part 10 from moving in the subject's body. For example, a part of the cable 11 may be fixed to a fixing part (not illustrated) that is fixed to a part of the tissue in the subject's body. Examples of the fixing part include a mouthpiece worn by the subject. By providing a mouthpiece with the fixing part, the extent to which the cable 11 is inserted into the subject's body can be kept within a predetermined range. Thus, the end part 10 can be stayed in the subject's body.

For another example, the container 10a of the end part 10 may be configured to expand so that it is appressed to the body tissue of the subject such as the esophagus. By appressing the container 10a to the body tissue, the end part 10 can be stayed at the body tissue. Although not illustrated, in such a configuration, the container 10a is formed to have a double-bag structure. The ultrasound transducer 12 is placed in the inner bag of the container 10a. The outer bag of the container 10a is connected to the cable 11. The cable 11 is communicated with the outer bag, so that fluid, i.e., liquid such as sterile water, gas such as air, and the like, can be injected from a pipe 11c (see FIG. 2B) in the cable 11. The container 10a expands with the injection of fluid, and contracts when the fluid is discharged. While the ultrasound transducer 12 is provided in the container 10a of the end part 10, whether other elements, such as the transmit-receive controller 14, the direction controller 16, and the drive unit 18, are provided to the end part 10 is determined as appropriate depending on the structure of the ultrasound transducer 12 (element array, etc.).

(Structure of Entire Ultrasonic Transducer and Each Component)

The ultrasound transducer 12 used in the end part 10 illustrated in FIG. 2B includes the rectangular ultrasound oscillators 12a, which are arranged in a circular array, i.e., 1D array (see FIG. 3A). In the ultrasound transducer 12, the ultrasound oscillators 12a are arranged all over the outer peripheral surface of the support (not illustrated). Hereinafter, the structure, where a back member, a back electrode, a piezoelectric element, a front electrode, and an acoustic matching layer are arranged on the support in layers, is referred to as the "ultrasound oscillators" 12a. In addition, a group of the support, the ultrasound oscillators 12a, and an acoustic lens 12c is referred to as the "ultrasound transducer" 12. The support (not illustrated) supports the ultrasound oscillators 12a. The support is, for example, formed in a cylinder, the inside of which is hollow along the central axis. The support may have a columnar form. If all the ultrasound oscillators 12a are required to be tilted to change the transmission direction of ultrasound waves (ultrasound beam angle, etc.), the support is connected to the drive unit 18. The ultrasound oscillators 12a are configured with the back member, the back electrode, the piezoelectric element, the front electrode, and the acoustic matching layer arranged radially in layers from the outer peripheral surface of the support toward the outside.

The piezoelectric element (not illustrated) is provided with the back electrode on a surface on the side of the back member (on the side of the support), and the front electrode on a surface on the opposite side (the side of the acoustic lens). The piezoelectric element converts a voltage applied to the front electrode and the back electrode into ultrasound waves. The ultrasound waves are transmitted to the subject. Having received reflected waves from the subject, the piezoelectric element converts the waves into voltage (echo signal). The piezoelectric element is generally made of such material as PZT (piezoelectric zirconate titanate/e.g., lead zirconate titanate/Pb(Zr, Ti)$O_3$). As the piezoelectric element, PVDF (polyvinylidene difluoride/polyvinylidene fluoride/($CH_2CF_2$)n) may be used. The use of a PVDF film as a piezoelectric element facilitates making the end part 10 because of its flexibility. Further, if a PVDF film is used as the piezoelectric element, the ultrasound oscillators 12a can be thinner in the layer direction, and thus the end part 10 can be downsized. Moreover, PVDF films possess good resistance to shock. As for other examples of the piezoelectric element, barium titanate ($BaTiO_3$), PZNT ($Pb(Zn_{1/3}Nb_{2/3})O_3$—$PbTiO_3$) single crystal, PMNT ($Pb(Mg_{1/3}Nb_{2/3})O_3$—$PbTiO_3$) single crystal, and the like may be used. The piezoelectric element may be of a single layer, or it may be multilayered.

Part of all the piezoelectric elements may be connected to a temperature sensing circuit (not illustrated). The piezoelectric element connected to the temperature sensing circuit is used as a pyroelectric element. The temperature sensing circuit detects the temperature around the ultrasound oscillators 12a based on a pyroelectric voltage value or a pyroelectric current value received from the pyroelectric element. The temperature sensing circuit may be located in the end part 10, or in the main body 101. Since the end part 10 is placed in the subject's body, it is effective in monitoring an observation site to enable the operator to know the temperature around the ultrasound oscillators 12a.

The acoustic matching layer is arranged adjacent to the front electrode on the acoustic lens 12c side in the front electrode of the piezoelectric element. Thus, the acoustic matching layer is located between the piezoelectric element and the acoustic lens 12c. The acoustic matching layer matches acoustic impedance between the piezoelectric element and the subject. There may be two or more acoustic matching layers arranged in the layer direction. In this case, materials that vary in acoustic impedance in stages are used for the acoustic matching layers. This structure achieves acoustic matching by changing acoustic impedance in stages between the piezoelectric element and the acoustic lens 12c.

The back member is arranged adjacent to the back electrode on the side of the support in the back electrode of the piezoelectric element. The back member absorbs ultrasound waves emitted to the opposite direction to their irradiation direction (backward) during ultrasound transmission, thereby suppressing the excessive oscillation of the piezoelectric element. The back member suppresses the reflection of ultrasound waves from the back surface of the piezoelectric element when the piezoelectric element is oscillating. Therefore, with the back member, it is possible to avoid adverse effect on transmitting/receiving of ultrasound waves. As the back member, based on the features including acoustic attenuation, acoustic impedance, and the like, any materials such as an epoxy resin containing PZT powder, tungsten powder, etc., rubber filled with polyvinyl chloride and/or ferrite powder, or porous ceramic impregnated with resin such as epoxy, and the like may be used.

<Acoustic Lens>

The acoustic lens 12c (see FIG. 2B) converges transmitted/received ultrasound waves and forms them into a beam shape. The acoustic lens 12c is made of such material as silicone having an acoustic impedance similar to the living body. If the ultrasound oscillators 12a are in a 2D array, and the ultrasound transducer 12 is capable of converging ultrasound waves into a beam by electronic scanning, the ultrasound transducer 12 may not include the acoustic lens 12c.

Figure 2C:
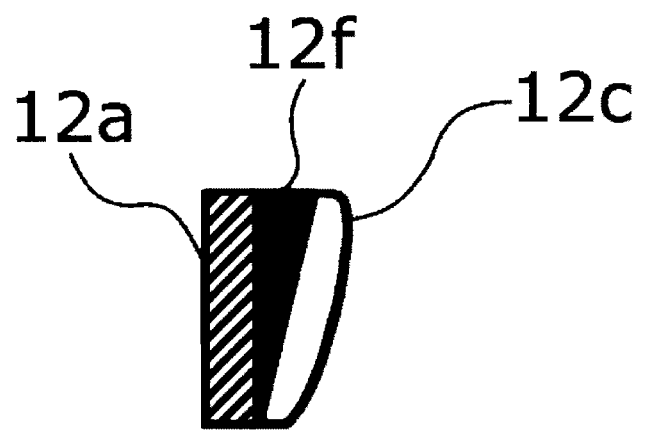
FIG. 2C is a schematic cross section of an ultrasound transducer illustrated in FIG. 2A, to which offset is applied.

When the end part 10 is inserted in the esophagus of the subject and the transmission direction of ultrasound waves is pointed to the heart, a wedge-shaped offset 12f may be added between the acoustic lens 12c and the ultrasound oscillators 12a as illustrated in FIG. 2C. By the addition of the offset 12f, the acoustic lens 12c is tilted to the support of the ultrasound oscillators 12a. With this structure, directions of ultrasound waves from the piezoelectric elements are converged into a different direction. Depending on the tilt angle of the offset 12f, it becomes unnecessary to perform drive control for transmitting ultrasound waves from the ultrasound oscillators 12a of the end part 10 placed in the esophagus to the heart. Alternatively, depending on the tilt angle, the drive control can be simplified.

In the structure illustrated in FIG. 3A, the direction controller 16 and the drive unit 18 (described later) tilt the ultrasound transducer 12 in response to an instruction signal on the transmission direction of ultrasound waves from the main body 101. By this tilting operation, the transmission direction of ultrasound waves is adjusted. If the offset 12f is provided, the tilting operation may not be necessary.

(Other Examples of Ultrasonic Transducer)

Figure 3B:
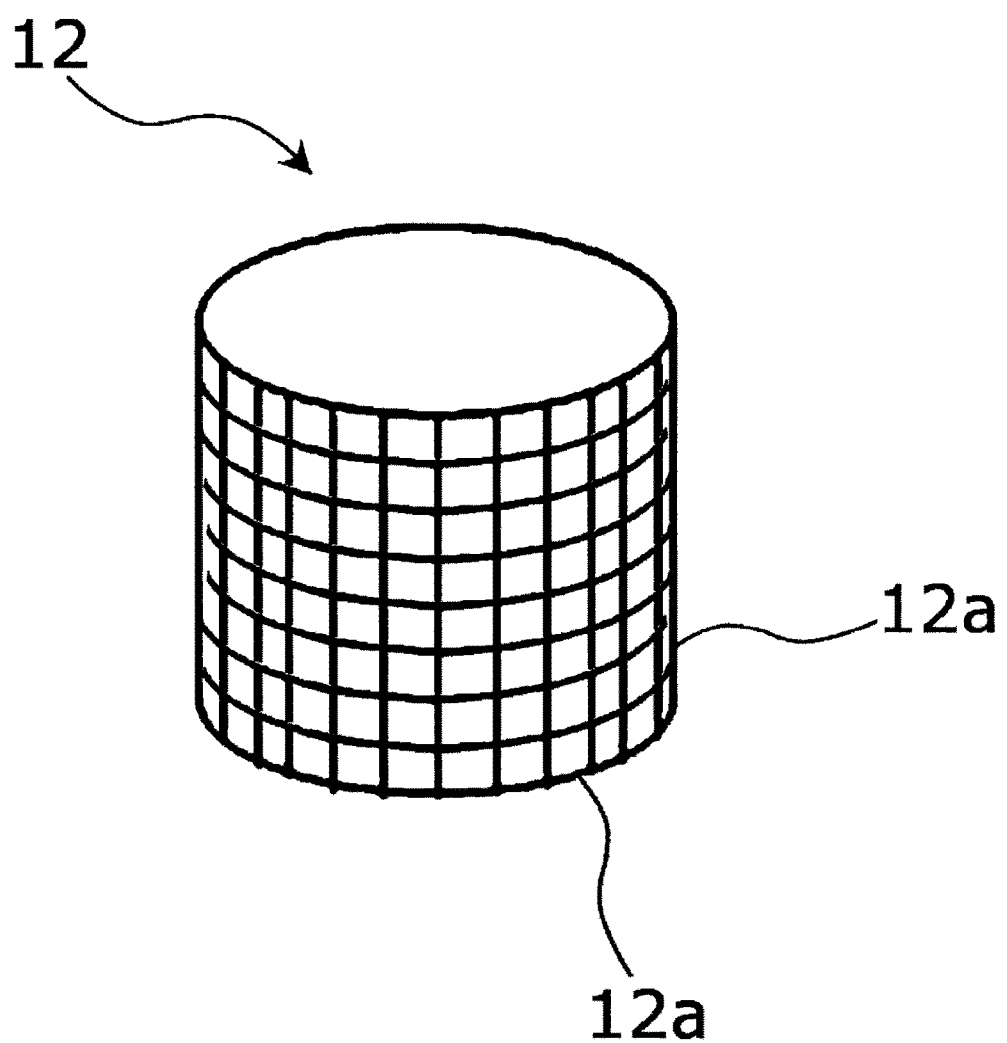
FIG. 3B is a schematic perspective view of the ultrasound transducer.
Figure 3C:
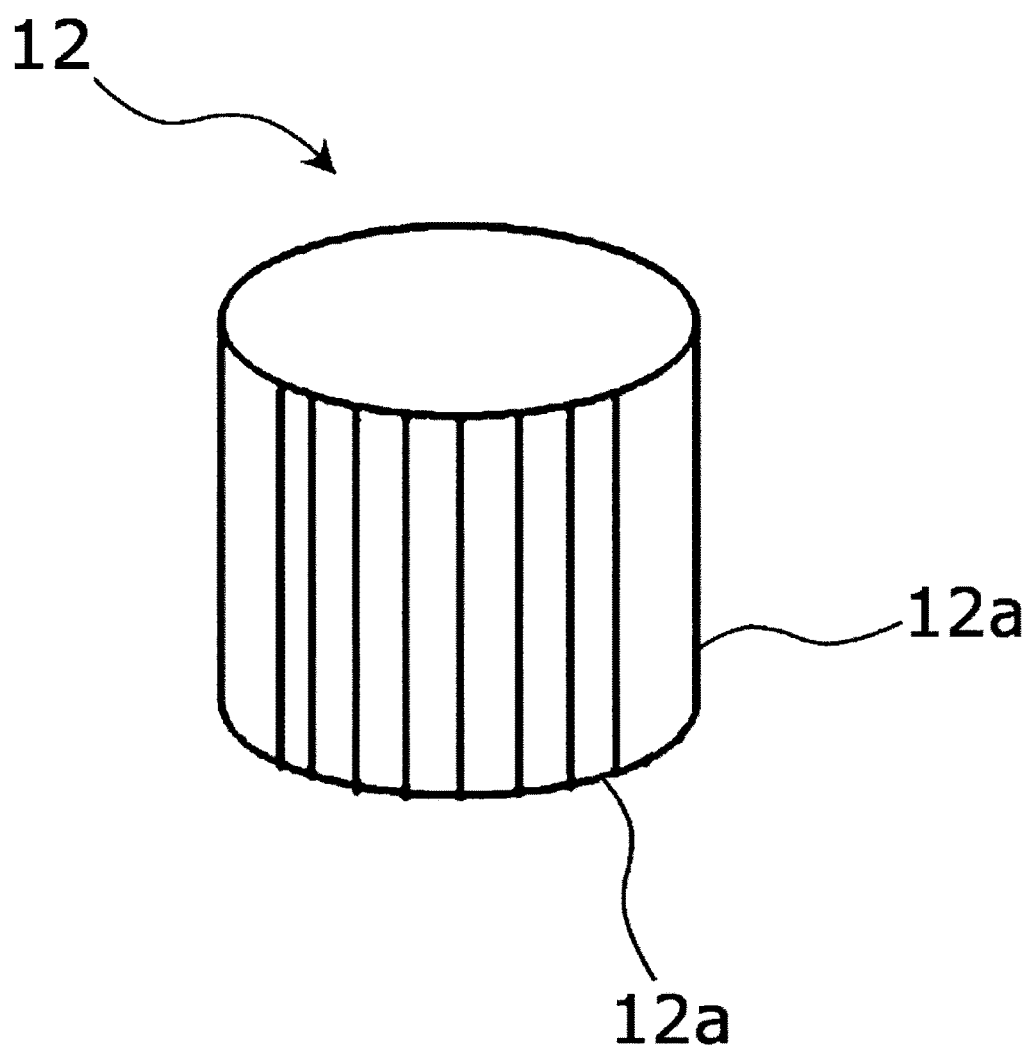
FIG. 3C is a schematic perspective view of the ultrasound transducer.
Figure 3D:
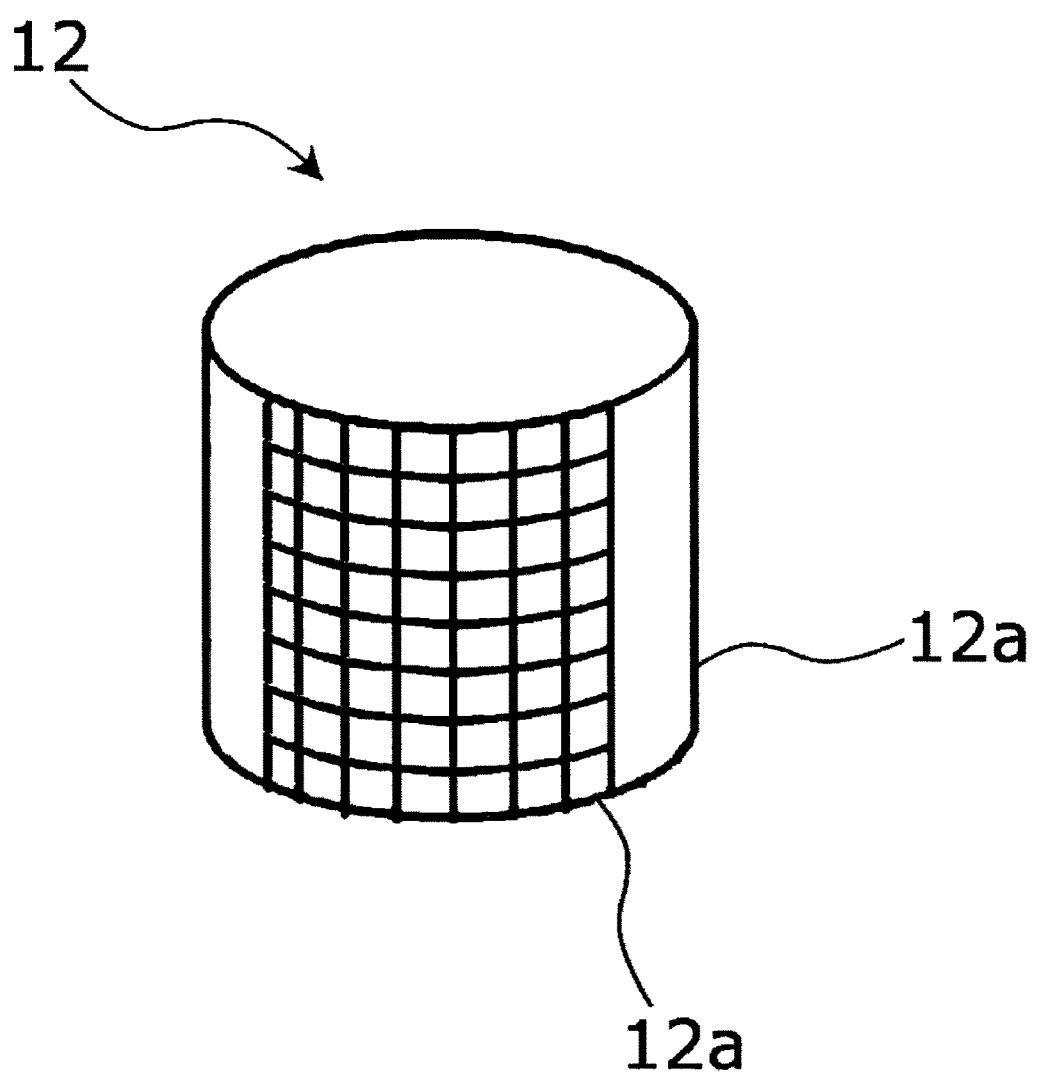
FIG. 3D is a schematic perspective view of the ultrasound transducer.

Referring to FIGS. 3B to 3D, other examples of the structure of the ultrasound transducer 12 are described. FIGS. 3B to 3D each illustrate a schematic perspective view of the ultrasound transducer 12. FIG. 3C illustrates the 1D array ultrasound transducer 12, while FIGS. 3B and 3D illustrate the 2D array ultrasound transducer 12. Besides, FIG. 3B illustrates the ultrasound transducer 12, in which the ultrasound oscillators 12a are provided all over the outer peripheral surface of the support. FIGS. 3C and 3D illustrate the ultrasound transducer 12, in which the ultrasound oscillators 12a are provided to a part of the outer peripheral surface of the support.

In the example of FIG. 3B, the ultrasound oscillators 12a are arranged in a 2D array all over the outer peripheral surface of the support. In this structure, the transmit-receive controller (described later) is capable of switching the ultrasound oscillators to be driven as well as deflecting and converging ultrasound waves (ultrasound beams) by electronic scanning. In the structure of the ultrasound transducer 12 illustrated in FIG. 3B, the transmit-receive controller 14 can deflect and converge ultrasound waves, by electronic scanning, not only in a direction in which the ultrasound oscillators are arrayed (azimuth direction), but also in the elevation direction substantially perpendicular to the direction. Accordingly, in this structure, there may be no need to rotate and tilt the ultrasound transducer 12. In this case, the structure does not include the direction controller 16 and the drive unit 18. The acoustic lens 12c may also not be included.

In the example of FIG. 3C, the ultrasound oscillators 12a are arranged in a 1D array in a part in the circumferential direction of the outer peripheral surface of the support. That is, for example, when the support is of a cylindrical form, the ultrasound oscillators 12a are arrayed in an area within a predetermined angle range (e.g., 60°) from the central axis in the circumferential direction of the outer peripheral surface. In this structure, upon receipt of an instruction signal from the main body 101, the direction controller 16 and the drive unit 18 (described later) perform rotating or tilting of the ultrasound transducer 12, or both.

In the example of FIG. 3D, the ultrasound oscillators 12a are arranged in a 2D array in a part in the circumferential direction of the outer peripheral surface of the support. In this structure, upon receipt of an instruction signal from the main body 101, the direction controller 16 and the drive unit 18 (described later) rotate the ultrasound transducer 12. The state that the ultrasound oscillators 12a are arrayed in a part means that, for example, when the support is of a cylindrical form, the ultrasound oscillators 12a are arrayed in the azimuth and elevation directions in an area within a predetermined angle range (e.g., 60°) from the central axis in the circumferential direction of the outer peripheral surface.

(Modification of End Part)

If the used as the piezoelectric element is among those having low acoustic impedance such as PVDF, the back member may be configured to reflect ultrasound waves radiated thereto instead of absorbing them. For example, a material that doubles as the back member and the support of the ultrasound oscillators 12a may be used. The use of a shape-memory alloy as the material enables the end part 10 having the following structure. The modification of the end part 10 is described below with reference to FIG. 2D.

Figure 2D:
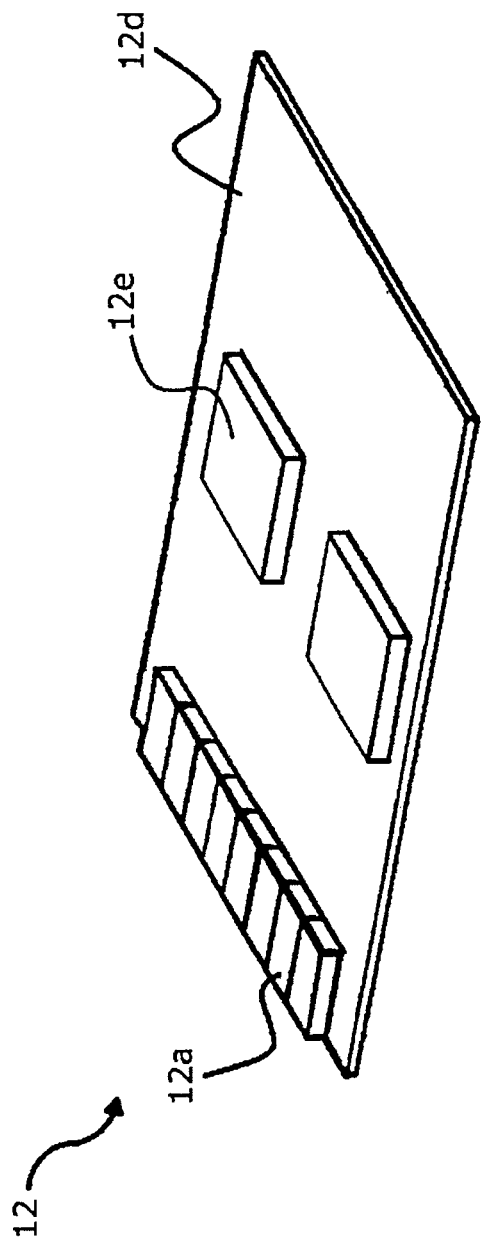
FIG. 2D is a schematic perspective view of a flexible printed circuit board.

The container 10a is configured such that the entire end part 10 is contracted when inserted into the subject's body. As illustrated in FIG. 2D, layers from the acoustic matching layer to the piezoelectric element are arranged on a flexible printed circuit (FPC) board 12d. On the FPC board 12d may be arranged an integrated circuit (IC) 12e having the function of the transmit-receive controller 14 and the like. The IC 12e has the function of the transmit-receive controller 14 and the like. The transmit-receive controller 14 is electrically connected to the electrode of the piezoelectric element via a pattern formed on the FPC board 12d and the like. The FPC board 12d is formed on the back member made of a shape-memory alloy.

The container 10a is configured such that, having been inserted in the subject's body, for example, when placed in the esophagus, the entire end part 10 is expanded by the injection of fluid such as air, water, and the like through the cable 11 (see FIG. 2B). When the container 10a is expanded, a predetermined space is formed therein. The shape-memory alloy as the back member is configured to recover, for example, cylindrical or columnar form as illustrated in FIG. 3A, when being expanded. By the discharge (suction, etc.) of fluid injected in the container 10a, the entire end part 10 is contracted.

The ultrasound transducer 12 is supported by the FPC board 12d and the back member made of a shape-memory alloy. Accordingly, in response to the contraction of the container 10a, the entire ultrasound transducer 12 is also contracted. With this structure, the end part 10 becomes smaller when being contracted. Thus, the operator can arbitrarily expand/contract the end part 10, and thereby can easily insert and remove the end part 10 into/from the subject's body.

(Transmit-Receive Controller)

Figure 4:
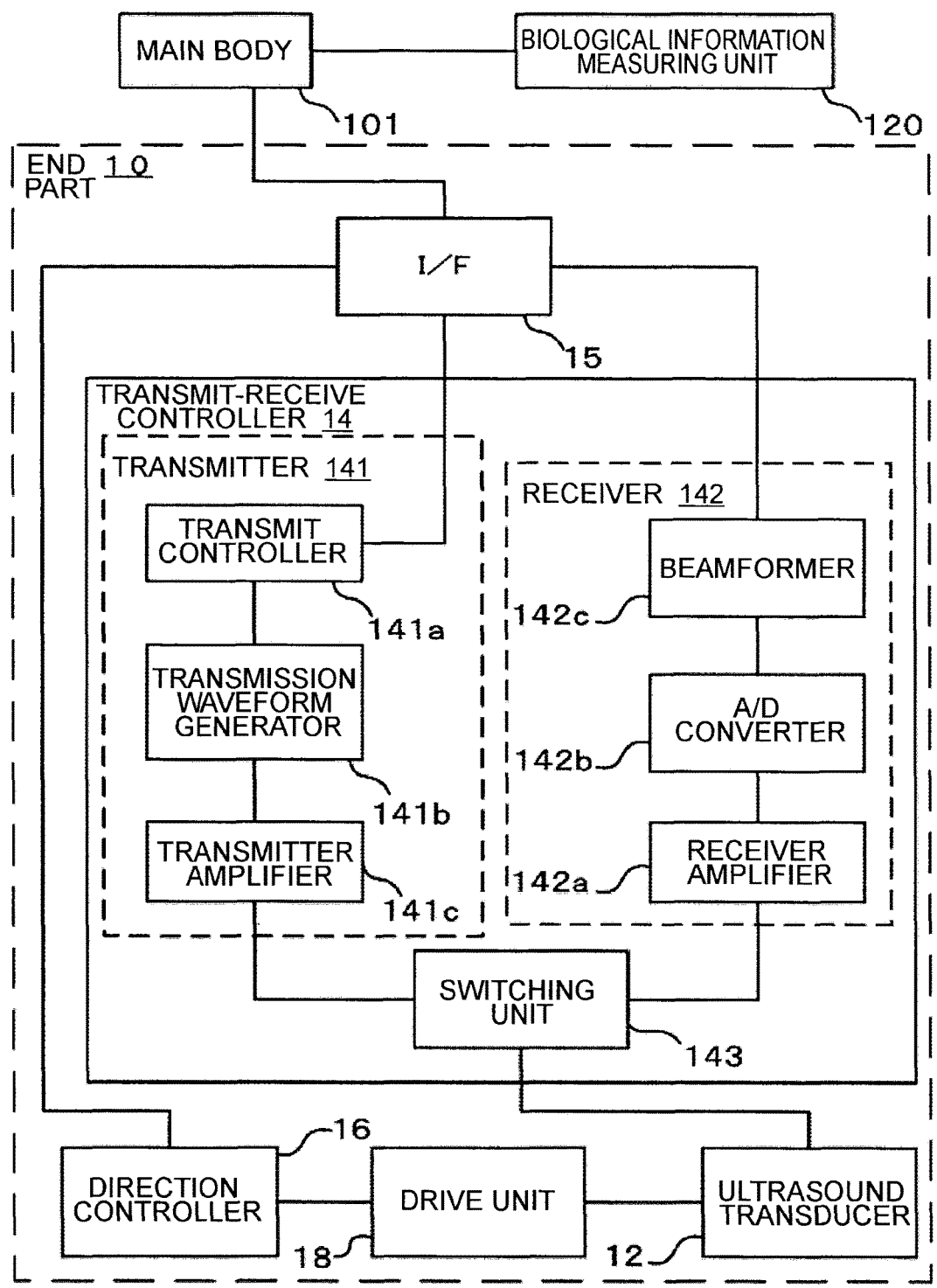
FIG. 4 is a schematic block diagram illustrating an example of the functional structure of an end part of an ultrasound diagnosis apparatus according to a first embodiment.

Referring next to FIG. 4, a description is given of the transmit-receive controller 14 of the end part 10. FIG. 4 is a schematic block diagram illustrating an example of the functional structure of the end part 10 of the ultrasound diagnosis apparatus 100 of the first embodiment. As illustrated in FIG. 4, the transmit-receive controller 14 includes a transmitter 141, a receiver 142, and a switching unit 143. They are each described below.

(Transmitter)

The transmitter 141 of the end part 10 includes a transmit controller 141a, a transmission waveform generator 141b, and a transmitter amplifier 141c. The transmitter 141 receives an instruction signal on the transmission of ultrasound waves from the main body 101 (a transmitter unit 105 or the like, see FIG. 5) through the I/F 15. The transmitter 141 further includes a clock generation circuit and a transmitter delay circuit (not illustrated). The transmit controller 141a controls the clock generation circuit, the transmitter delay circuit, and the like. The clock generation circuit generates clock signals for determining the transmission frequency and the transmission timing of ultrasound waves. For example, the clock generation circuit feeds the transmitter delay circuit with a reference clock signal. The transmitter delay circuit sends the transmission waveform generator 141b a drive signal having a predetermined delay time. The predetermined delay time is determined based on the transmission focal point of ultrasound waves.

The transmission waveform generator 141b includes, for example, a pulser circuit (not illustrated). The pulser circuit includes therein as many pulsers as individual channels corresponding to the ultrasound oscillators 12a, and generates transmission drive pulses. The pulser circuit repeatedly generates a rate pulse at a predetermined pulse repetition frequency (PRF). The rate pulses are distributed into the number of the channels, and sent to the transmitter delay circuit.

The transmitter delay circuit of the transmit controller 141a provides the rate pulse with a transmission delay time related to the transmission direction and the transmission focus. Transmission drive pulses are generated at timing based on the rate pulses each being delayed. The transmission drive pulses are amplified by the transmitter amplifier 141c, and sent to the switching unit 143. As described above, the transmitter delay circuit provides the rate pulse with a transmission delay time to focus ultrasound waves for transmission (to converge ultrasound waves into a beam). With this, the transmission directivity of the ultrasound waves is determined. In addition, the transmitter delay circuit changes the transmission delay time to be given to each rate pulse, thereby controlling the transmission direction of ultrasound waves from the ultrasound wave radiation surfaces of the ultrasound oscillators 12a.

(Switching Unit)

The switching unit 143 controls switching between the transmitter 141 and the receiver 142. The switching unit 143 has a switch relating to transmitting/receiving of ultrasound waves. If scan mode on the main body 101 side is set to continuous wave Doppler (CWD) mode, as described below, the switching unit 143 connects some elements of the ultrasound oscillators 12a to the transmitter 141 for transmission, and connects some others to the receiver 142 for reception.

If the scan mode on the main body 101 side is set to perform B (brightness) mode and pulsed wave Doppler (PWD) mode in parallel, the switching unit 143 alternately repeats control to sequentially switch elements to be driven according to the B mode and control to switch to elements that transmit ultrasound waves toward a set sample volume (sampling gate). In the B mode, a group of elements to be driven is shifted in the element array direction to control the transmission direction of ultrasound waves or the like.

Besides, the switching unit 143 switches sub-arrays each including a group of elements in m rows x n columns (a group of oscillators) in the 2D array ultrasound transducer 12. A transmission drive pulse from the transmitter amplifier 141c is applied to each element of the sub-array connected to the switch of the switching unit 143, and the piezoelectric element is driven.

(Receiver)

The receiver 142 of the end part 10 receives echo signals corresponding to ultrasound waves reflected from the subject. The receiver 142 amplifies the echo signals received by the ultrasound transducer 12, and also adds delay thereto. By the delay addition of the receiver 142, the analog echo signals are converted to digital data having been subjected to phasing (i.e., subjected to beam forming). Specific examples are as follows.

The receiver 142 includes a receiver amplifier 142a, an A/D converter 142b, and a beamformer 142c. The receiver 142 may further include a sub-array beamformer (not illustrated). The receiver amplifier 142a amplifies echo signals received from the ultrasound transducer 12 with respect to each receiver channel. The A/D converter 142b converts the amplified echo signals to digital signals. Having been converted into digital signals, the echo signals are each stored in a digital memory (not illustrated). The digital memory is provided for each channel (or each element). Each echo signal is stored in the corresponding digital memory. The echo signal is also stored in an address corresponding to the time it is received. The A/D converter 142b is capable of thinning out data that has been filtered according to the bandwidth of the echo signal. If the receiver 142 has the sub-array beamformer (not illustrated), the sub-array beamformer can add echo signals from adjacent elements in the ultrasound oscillators 12a.

The beamformer 142c provides the echo signals each converted into a digital signal with a delay time required to determine the reception directivity. The reception delay time is calculated for each element. The beamformer 142c adds up the echo signals having the delay time. The beamformer 142c reads each of the echo signals from the digital memory as appropriate based on the required delay time calculated, and adds up them. The beamformer 142c repeats this addition while changing a reception focus position along the transmission beam. The beamformer 142c emphasizes a reflection component from a direction corresponding to the reception directivity. The received beam signal processed by the receiver 142 is sent to a signal processor (a B-mode signal processing unit 107, a Doppler signal processing unit 108) via the I/F 15, a receiver unit 106, or the like.

(Direction Controller, Drive Unit)

In response to an instruction signal on the transmission direction of ultrasound waves from the main body 101, the direction controller 16 controls the drive unit 18. For example, the direction controller 16 drives the drive unit 18 to change the angle or orientation of the radiation surface of the ultrasound waves according to ROI (Region of Interest) set on the main body 101 side. The drive unit 18 is comprised of, for example, a micro-actuator such as an ultrasound motor. The drive unit 18 is driven under the control of the direction controller 16. The drive unit 18 is connected to the ultrasound transducer 12. With this structure, when the drive unit 18 is driven, the ultrasound transducer 12 is rotated or tilted. Thus, by driving the drive unit 18, the transmission direction of ultrasound waves can be changed in the ultrasound transducer 12.

<Structure of Main Body>

Figure 5:
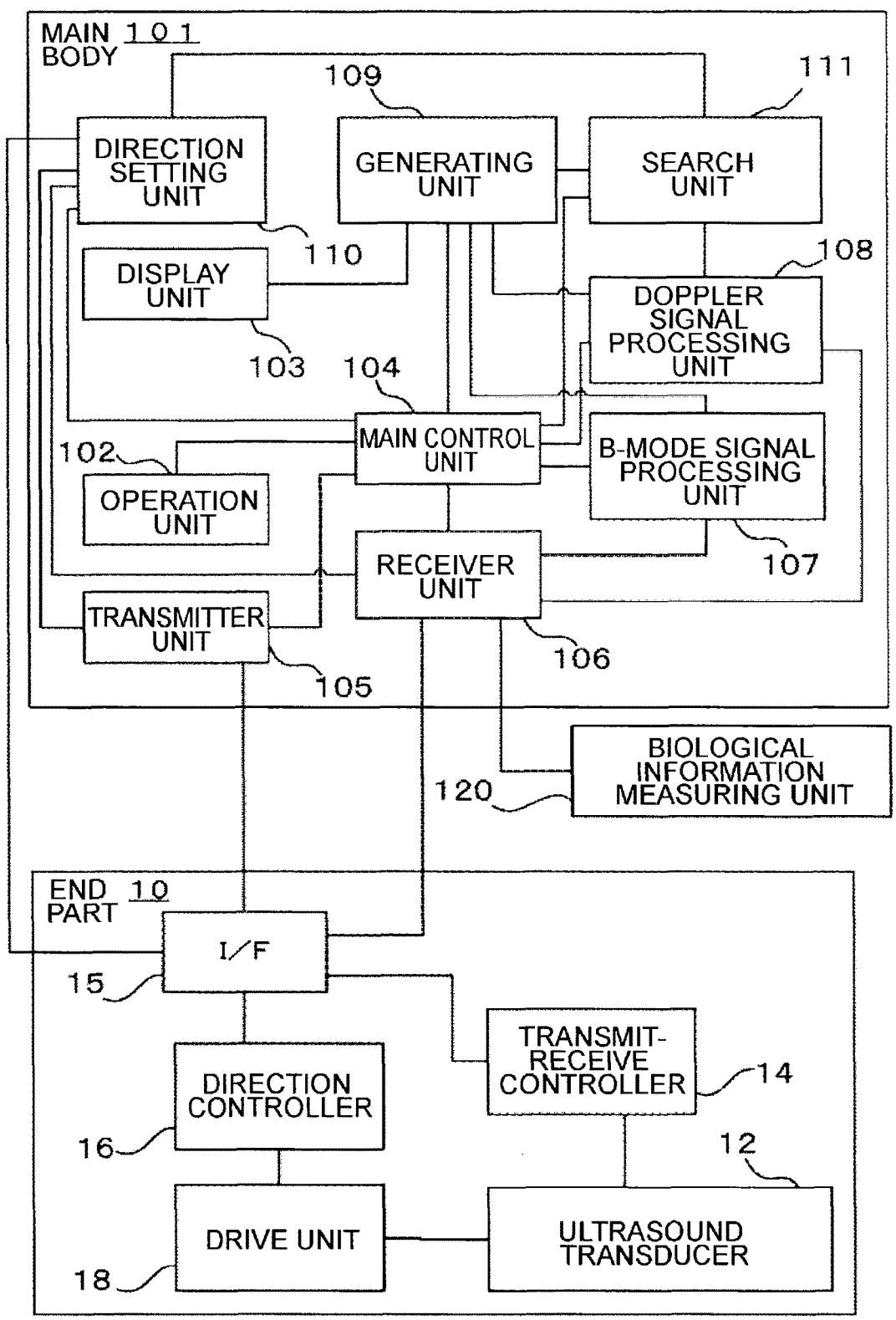
FIG. 5 is a schematic block diagram illustrating an example of the functional structure of a main body of the ultrasound diagnosis apparatus of the first embodiment.

Next, the control and the operation of each part of the main body 101 are described with reference to FIG. 5. The ultrasound diagnosis apparatus 100 illustrated in FIG. 5 is, for example, used to obtain such images as those indicating the form of biological tissues such as the heart (see FIG. 6) and those indicating the state of blood flow (see FIG. 7A). As illustrated in FIG. 5, in the ultrasound diagnosis apparatus 100, the main body 101 is connected to the end part 10 and a biological information measuring unit 120. The end part 10 corresponds to an example of "ultrasound transmitter/receiver". FIG. 5 is a schematic block diagram illustrating an example of the functional structure of the main body 101 of the ultrasound diagnosis apparatus of the first embodiment.

The main body 101 includes therein units for performing input/output operations, calculations, controls, and the like of the ultrasound diagnosis apparatus 100 (see FIG. 5). In FIG. 5, the main body 101 includes, as the functional units, the operation unit 102, the display unit 103, a main control unit 104, the transmitter unit 105, the receiver unit 106, the B-mode signal processing unit 107, the Doppler signal processing unit 108, a generating unit 109, a direction setting unit 110, and a search unit 111. Incidentally, the biological information measuring unit 120 may be included in the configuration of the ultrasound diagnosis apparatus 100. The main body 101 may include a power supply connected to the end part 10 via the cable 11.

(Operation Unit)

In response to operation by the operator, the operation unit 102 feeds signals and information corresponding to the operation to each unit. Examples of the operation unit 102 are not limited to a keyboard and a pointing device such as a mouse, but may include any other user interfaces. For example, the function of the operation unit 102 for inputting signals and information may be implemented as a software keyboard (softkey) on the touch panel integrated with the display unit 103. The operation unit 102 may have a function of receiving input of signals and information via media and networks. Note that, in the following, the ultrasound image includes not only anatomical images such as B-mode images but also waveform images based on the motion information of tissues and blood flow and color display images of brightness and color based on the motion information of tissues and blood flow.

If, for example, the operator operates a FREEZE button or an end button on the operation unit 102, transmitting/receiving of ultrasound waves is paused or terminated, respectively. The operator can select scan mode of ultrasound waves by operating the operation unit 102. Using the operation unit 102, the operator can select scan mode relating to transmitting/receiving of ultrasound waves and determine the initial setting. The operator can also specify sample volume (sampling gate) in Doppler mode through the operation unit 102. Further, the operator can determine the settings for monitoring biological information such as cardiac ejection fraction through the operation unit 102.

(Display Unit)

The display unit 103 displays ultrasound images as well as operation screens, setting screens, and the like. Examples of the display unit 103 include any display devices such as a cathode ray tube (CRT), a liquid crystal display (LCD), a plasma display panel, an organic electroluminescent display (OELD), a field emission display (FED), and the like.

(Main Control Unit)

The main control unit 104 includes CPU (Central Processing Unit), ROM (Read Only Memory), RAM (Random Access Memory), and the like. The CPU loads a control program into the RAM as appropriate, and thereby the main control unit 104 functions as a controller that controls each part of the main body 101. That is, the main control unit 104 controls each part in the main body 101 as follows.

(Transmitter Unit)

The transmitter unit 105 of the main body 101 transmits a signal related to the driving of the ultrasound transducer 12 to the transmit-receive controller 14 of the end part 10 according to selected scan mode. For example, the main control unit 104 receives a selection operation of scan mode (scan sequence) through the operation unit 102. In response to this operation, the main control unit 104 controls the transmitter unit 105 depending on the selected scan mode. According to the selected scan mode, transmission frequency, transmission driving voltage, and the like are changed. As the scan mode, such modes as follows can be selected: B-mode, power Doppler mode (PDI; Power Doppler Imaging), pulsed Doppler mode, continuous wave Doppler mode, color Doppler mode (CDI; Color Doppler Imaging/CFM; Color Flow Mapping), tissue Doppler mode (TDI; Tissue Doppler Imaging), M (motion) mode, and the like. In addition, any combination of them is also selectable for the scan mode.

In the pulsed Doppler mode, the direction of transmission beams and transmission focal point (range related to the depth direction and the position of an observation area) are set based on the sample volume (sampling gate). The sample volume is, for example, set via the direction setting unit 110 by the operator specifying any range on a displayed B-mode image using the operation unit 102. In the continuous wave Doppler mode, a region of space occupied by transmission beams is the observation area.

When the search unit 111 performs a search process, according to the elapse of predetermined time, in any of the above Doppler modes, the transmitter unit 105 sends the transmitter 141 of the end part 10 a control signal for obtaining information on the motion of a tissue and blood flow in an observation site inside the subject's body. In this process, the transmission direction of ultrasound waves in the Doppler mode is changed according to a predetermined trigger. The details are described in the explanation of the search unit 111.

(Receiver Unit)

From the end part 10, the receiver unit 106 of the main body 101 receives a digital echo signal (received beam signal) having been subjected to predetermined processing by the receiver 142. The echo signal is sent to the signal processor (the B-mode signal processing unit 107, the Doppler signal processing unit 108).

(Signal Processor; B-Mode Signal Processing Unit)

The signal processor includes the B-mode signal processing unit 107 and the Doppler signal processing unit 108. Having received the received beam signal from the receiver unit 106, the B-mode signal processing unit 107 creates a visual image of amplitude information of the signal. Specifically, the B-mode signal processing unit 107 performs band-pass filtering on the received beam signal, then detects the envelope of the received beam signal after the band-pass filtering, and compresses detected data by logarithmic transformation. Thus, the B-mode signal processing unit 107 generates RAW data of a B-mode image.

(Signal Processor; Doppler Signal Processing Unit)

As Doppler processing, the Doppler signal processing unit 108 detects Doppler shift frequency component by quadrature detection of the received beam signals, and performs fast Fourier transform (FFT). The Doppler signal processing unit 108 extracts a Doppler shift by the frequency analysis of the received beam signal (Doppler signal). The Doppler signal processing unit 108 extracts, based on the Doppler shift, contrast medium echo component as well as blood flow and tissues caused by Doppler effect, and generates RAW data of a Doppler image extracting mobile object information such as average velocity, variance, and power with respect to a plurality of points.

The Doppler signal processing unit 108 may be configured to perform color Doppler processing. The blood flow information is visualized by the color Doppler processing. The blood flow and tissue motion information includes velocity, distribution, and power. For example, the Doppler signal processing unit 108 processes the received beam signal, thereby generating RAW data of a color flow mapping (CFM) image in the region of interest. In particular, the Doppler signal processing unit 108 performs quadrature detection of the received beam signal from the receiver unit 106. The Doppler signal processing unit 108 then performs frequency analysis on the echo signal after the quadrature detection by autocorrelation method. By the frequency analysis, the Doppler signal processing unit 108 calculates the variance and the average velocity of blood flow at each point of the sample. The Doppler signal processing unit 108 generates the RAW data of the color flow mapping image representing the calculated variance and the average flow velocity by color. The Doppler signal processing unit 108 also calculates the power of blood flow based on the received beam signal subjected to the quadrature detection. The Doppler signal processing unit 108 generates the RAW data of the color flow mapping image representing the calculated power by color.

The signal processing units send the RAW data (ultrasound raster data) subjected to the signal processing to the generating unit 109. Incidentally, the B-mode signal processing unit 107 and the Doppler signal processing unit 108 of the embodiment can process both two-dimensional echo data and three-dimensional echo data.

(Generating Unit)

Figure 6:
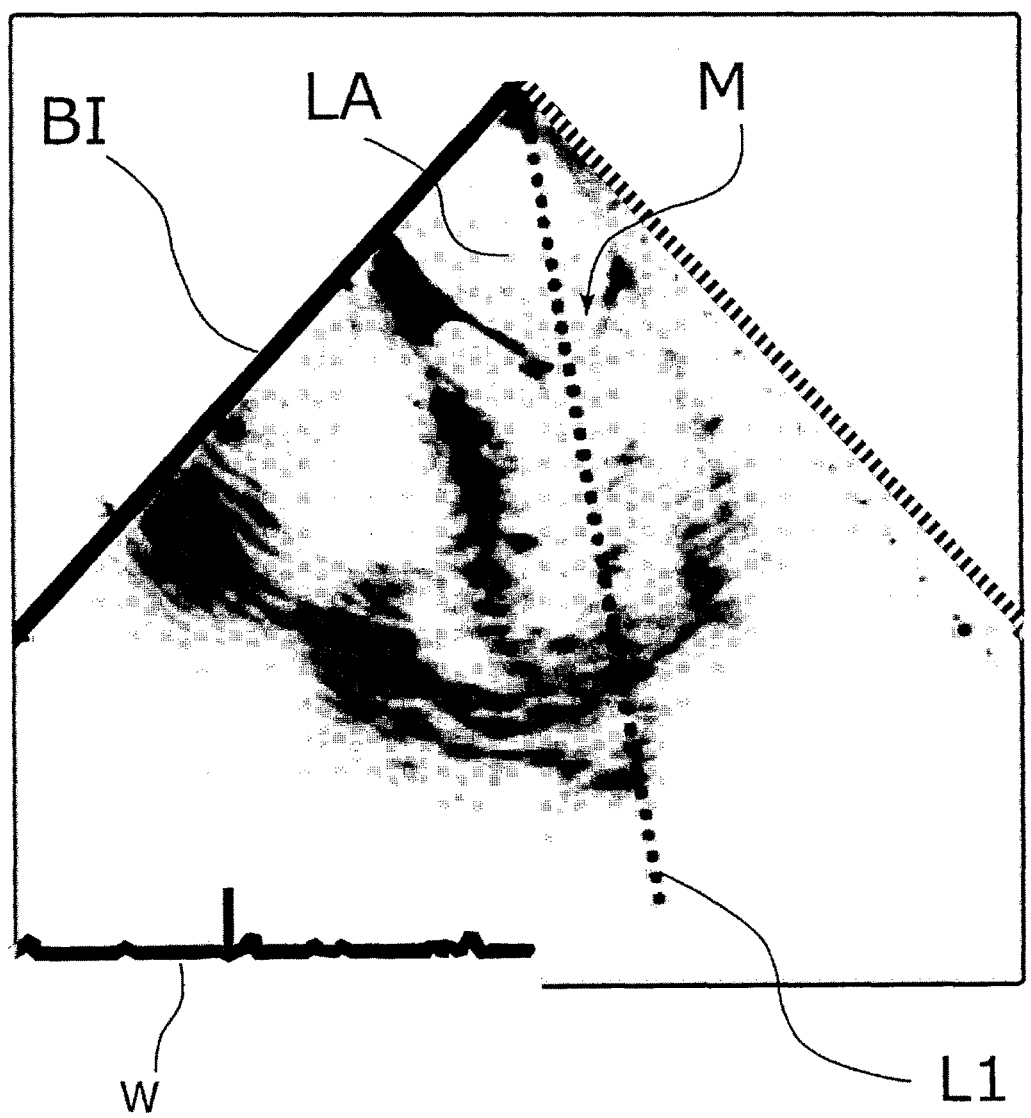
FIG. 6 is a schematic diagram of an example of a B-mode image generated by a generating unit of the first embodiment.
Figure 8:
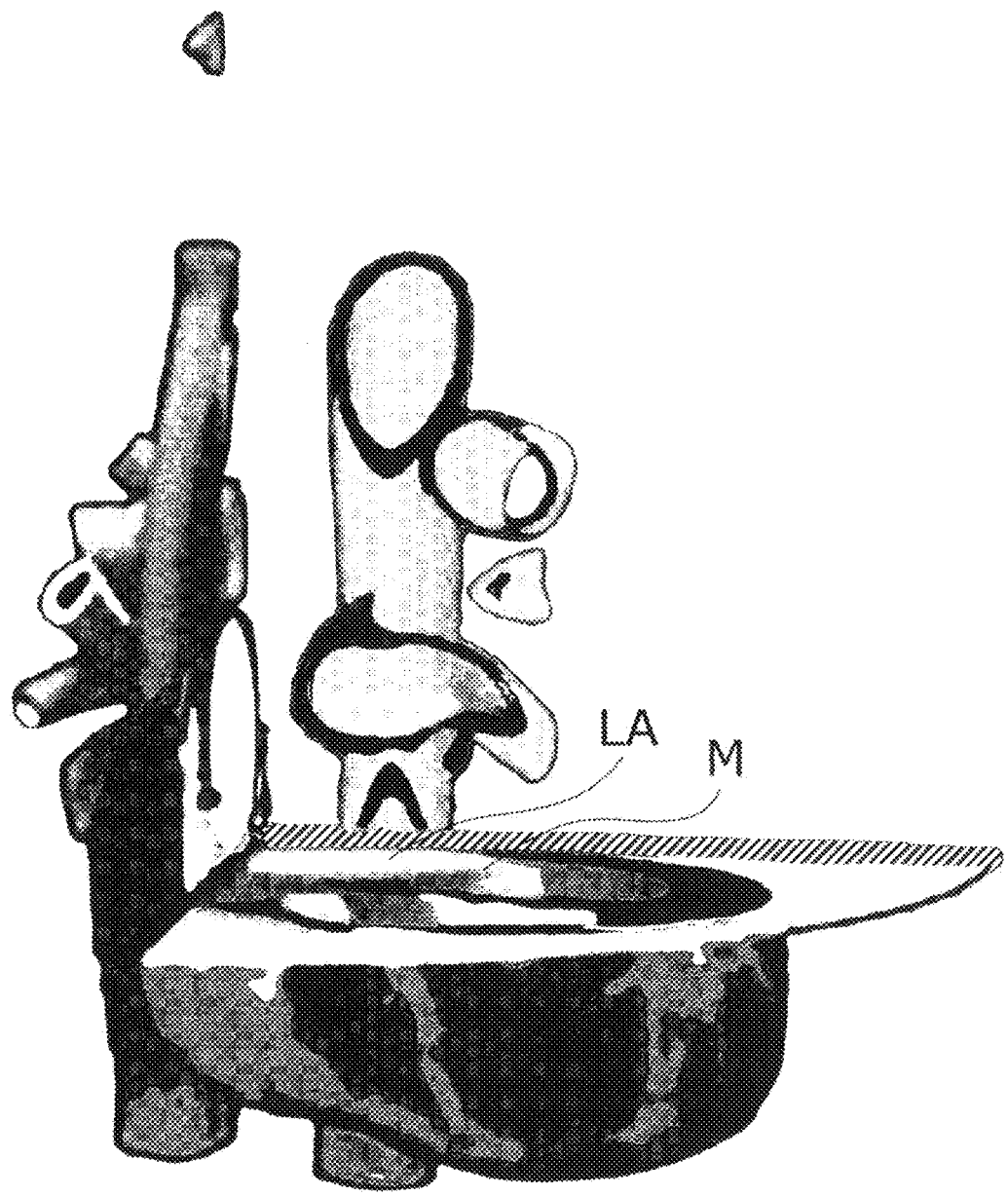
FIG. 8 is a schematic diagram illustrating a positional relationship for obtaining the B-mode image illustrated in FIG. 6.

With reference to FIGS. 6, 7A, 7B, and 8, the operation of the generating unit 109 is described. FIG. 6 is a schematic diagram of an example of a B-mode image generated by the generating unit 109 of the first embodiment. FIG. 7A is a schematic diagram of an example of a Doppler spectrum image generated by the generating unit 109. FIG. 7B is a schematic diagram of an example of the Doppler spectrum image illustrated in FIG. 7A displayed in parallel with ECG (electrocardiogram) waveform W fed by the biological information measuring unit 120. FIG. 8 is a schematic diagram of screen data illustrating a positional relationship for obtaining the cross section of the B-mode image illustrated in FIG. 6.

The generating unit 109 generates ultrasound image data based on the RAW data after the signal processing output from the signal processor (the B-mode signal processing unit 107, the Doppler signal processing unit 108). The generating unit 109 includes, for example, DSC (Digital Scan Converter). The generating unit 109 converts the RAW data subjected to the signal processing represented by a signal sequence of a scan line into image data represented by a Cartesian coordinate system (scan conversion). For example, by applying the scan conversion to the RAW data subjected to the signal processing by the B-mode signal processing unit 107, the generating unit 109 generates B-mode image data representing signal strength by brightness for each form of the tissues of the subject (see FIG. 6). As illustrated in FIG. 8, FIG. 6 is a four-chamber cross-sectional view, approached from the esophagus. FIG. 6 illustrates left atrium LA, mitral valve M, and a broken line L1 indicating the transmission direction of ultrasound waves. FIG. 6 also illustrates ECG waveform W.

Besides, the generating unit 109 performs coordinate transformation on the RAW data having undergone the color Doppler processing or the Doppler processing, and generates data of the Doppler image and data of the color flow mapping image that can be displayed on the display unit 103. For example, based on the result of the frequency analysis of the Doppler signal (echo signal) using FFT (Fast Fourier Transform) by the Doppler signal processing unit 108, the generating unit 109 generates a Doppler spectrum image where the velocity information of the mobile object (velocity information of blood flow, tissues, etc.) is drawn along the time series (see FIG. 7A).

In FIG. 7A, the vertical axis indicates frequency f (velocity v), while the horizontal axis indicates time t, and thus the spectrum is represented (FFT display). Additionally, in the waveform display, the line width represents the magnitude of the velocity, and the brightness represents the strength of the Doppler spectrum (corresponding to the power of the Doppler signal). In FIG. 7A, the tone is displayed in reverse to enhance the viewability of the image (the same is applied to FIG. 7B).

After ultrasound waves are transmitted/received with time through the end part 10, Doppler spectrum images are sequentially generated by the generating unit 109 through the above processing. The display unit 103 sequentially displays the generated images, and thus the state that the frequency f (the velocity v of the object) changes from moment to moment is displayed as a pattern.

The generating unit 109 can obtain ECG waveform from the biological information measuring unit 120 connected to the main body 101 via the main control unit 104 and the receiver unit 106. As illustrated in FIG. 7B, based on the ECG waveform W, the generating unit 109 generates an image capable of representing the Doppler spectrum image and the ECG waveform W synchronously in parallel.

Also, for example, from the RAW data of the color flow mapping image, the generating unit 109 generates color flow mapping images as an average velocity image indicating mobile object information (blood flow information, tissue motion information, etc.) a variance image, a power image, and a combination of these. The generating unit 109 may generate a composite image by combining any images from the B-mode image, the color flow mapping image, and the Doppler image. For example, the generating unit 109 generates a color flow mapping image by superimposing a color display image based on the motion information of tissues and blood flow on the B-mode image (or MPR (Multi-Planar Reconstruction) image) as well as generating a Doppler spectrum image by pulsed Doppler mode. Further, the generating unit 109 can generate an image capable of representing the color flow mapping image and the Doppler spectrum image in parallel with the ECG waveform based on the ECG waveform obtained from the biological information measuring unit 120.

When a volume data processing unit (not illustrated) is provided to the signal processor of the main body 101, the generating unit 109 may also display a volume rendering image and an MPR image. In this case, based on the echo signal received by the ultrasound transducer 12, the signal processor generates volume data representing the three-dimensional shape of tissues in the subject's body. Further, for example, the signal processor performs volume rendering on the volume data, thereby generating RAW data. Having obtained the RAW data after the volume rendering from the signal processor, the generating unit 109 generates a volume rendering image. The generating unit 109 can also generate an MPR image from the volume data.

(Direction Setting Unit)

The direction setting unit 110 sets the transmission direction of ultrasound waves by the ultrasound transducer 12 in the end part 10. The transmission direction is set based on operator's operation on the operation unit 102 or transmission direction data received from the search unit 111 (described later). The direction setting unit 110 sends the transmit-receive controller 14 or the direction controller 16 of the end part 10 determined transmission direction data. The direction setting unit 110 includes a storage unit (not illustrated) to store sample volume and the transmission direction data.

With respect to the setting of the transmission direction of ultrasound waves, the direction setting unit 110 receives such operations as selecting scan mode, setting sample volume, rotating/tilting the ultrasound transducer 12, and the like. The direction setting unit 110 also sets elements (or channels) to apply a drive signal in the ultrasound transducer 12 of the end part 10 depending on scan mode (continuous wave Doppler mode, etc.). As for the process of setting the transmission direction in response to the transmission direction data from the search unit 111, a description is given in the explanation of the search unit 111.

The information set for the transmission direction of ultrasound waves according to scan mode selection and sample volume setting (elements to be driven, angle/direction with respect to the ultrasound wave radiation surface, etc.) is sent to the transmit-receive controller 14 of the end part 10 via the transmitter unit 105. The information set for the transmission direction of ultrasound waves according to the rotation/tilting of the ultrasound transducer 12 (the amount of rotation, the tilt angle of the ultrasound transducer 12, etc.) is sent to the direction controller 16 of the end part 10. Incidentally, the direction setting unit 110 corresponds to an example of a "changer". Besides, in combination with the direction controller 16 and the drive unit 18 of the end part 10, the direction setting unit 110 corresponds to an example of a "changer". In combination with the transmitter unit 105 and the transmit-receive controller 14 of the end part 10, the direction setting unit 110 corresponds to an example of a "changer". With the structure described above, these examples of the "changer" can change the transmission direction of ultrasound waves.

(Search Unit)

While the ultrasound diagnosis apparatus 100 is transmitting/receiving ultrasound waves to obtain an ultrasound image, for adjusting the transmission direction of the ultrasound waves and the position of an area to be examined, the search unit 111 searches for the transmission direction of the ultrasound waves. The search is based on a Doppler signal obtained by transmitting/receiving ultrasound waves in the Doppler mode. Specifically, the search is performed by determining whether the transmission direction of ultrasound waves in the Doppler signal (or sample volume) adjusts to the desired observation object that produces a blood flow. When the adjustment is performed by the search unit 111 as a precondition, if any scan mode is selected by the operator, the main control unit 104 controls the end part 10 to acquire the Doppler signal in parallel with the acquisition of the ultrasound image. Note that the Doppler signal indicates an echo signal obtained in the Doppler mode, or the RAW data of the Doppler image having subjected to the signal processing by the signal processor. For convenience of the description, the Doppler signal may be similarly described below. In addition, the Doppler mode indicates any one of scan modes for obtaining blood flow information, including pulsed Doppler mode, continuous wave Doppler mode, color Doppler mode, power Doppler mode, and the like. For convenience of the description, the Doppler mode may be similarly described below.

For example, while the B-mode is selected and a B-mode image is generated, the main control unit 104 prompts the operator to set sample volume to be superimposed on the B-mode image displayed. When sample volume is set by the operator, according to a control signal received from the transmitter unit 105, the end part 10 alternately repeats B-mode scanning and the acquisition of Doppler signals in the pulsed Doppler mode. Based on the Doppler signals acquired, the search unit 111 performs the search process for the adjustment of the transmission direction of ultrasound waves and the position of an area to be examined. For example, the search unit 111 can be used to search for the transmission direction of ultrasound waves in the ultrasound transducer 12 upon monitoring cardiac ejection fraction.

Comparing pieces of signal strength information indicating the strength of Doppler signals obtained over time, the search unit 111 of the first embodiment determines the transmission direction of ultrasound waves with the highest signal strength. The transmission direction thus obtained corresponds to the direction of ultrasound beams being transmitted/received toward the observation site. Described below is an example of the search process performed by the search unit 111.

<<Start of Transmission of Ultrasonic Waves>>

After the end part 10 is inserted in the subject's body and scan mode is selected by the operator for preparation, the transmission of ultrasound waves is started. The receiver unit 106 of the main body 101 acquires echo signals based on the scan mode over time. The signal processor, the generating unit 109, and the like generate ultrasound images corresponding to the scan mode based on the echo signals. The display unit 103 displays the ultrasound images as appropriate. If the Doppler mode is selected as scan mode, only echo signals based on the selected scan mode are obtained. In this case, switching of the scan mode is not performed.

<<Start of Search>>

In the B mode, the B-mode signal processing unit 107 sends RAW data based on the echo signals to the generating unit 109. The Doppler signal processing unit 108 sends Doppler signals to the search unit 111. The transmitter unit 105 of the main body 101 starts transmitting ultrasound waves in the Doppler mode for the search process of the search unit 111. Triggered by the elapse of a predetermined time (any time that is set) from the start of the transmission, the transmitter unit 105 makes the end part 10 transmit ultrasound waves in the Doppler mode. At this time, the direction setting unit 110 sets the transmission direction so that the end part 10 transmits ultrasound waves not only in the direction in which ultrasound waves are transmitted first, but it transmits ultrasound waves while changing the transmission direction. The time interval at which the search process is performed can be set arbitrarily.

<<Ultrasonic Transmission Based on ECG Waveform>>

In the search process, ultrasound waves can be transmitted while the transmission direction is changed at any time interval set by the operator. For example, based on ECG waveform received from the biological information measuring unit 120, the main control unit 104 obtains predetermined cardiac time phase (diastole phase, etc.). The main control unit 104 may send the transmitter unit 105 a control signal related to the transmission timing of ultrasound waves with respect to each cardiac time phase thus obtained. The predetermined cardiac time phase refers to diastole or systole, early systole, mid-systole, late systole, early diastole, mid-diastole, late diastole or the like. Note that, in the search process, the main control unit 104 is not necessarily configured to transmit a control signal related to the transmission timing of ultrasound waves in the predetermined cardiac time phase. For another example, the main control unit 104 may be configured to obtain the predetermined cardiac time phase from ECG waveform received from the biological information measuring unit 120, and determine the signal strength (described later) of a Doppler signal in the time corresponding to the predetermined cardiac time phase among Doppler signals acquired successively.

Also when the search unit 111 performs the search process, the initial setting of the Doppler mode is required. For example, the main control unit 104 notifies the operator of the start of selected scan mode, or prompts the operator to set sample volume before or after it. As the notification, for example, a predetermined character string may be displayed on the display unit 103, or voice guidance may be output. After a predetermined time has elapsed, first, the direction setting unit 110 makes the end part 10 transmit ultrasound waves via the transmitter unit 105 in the transmission direction corresponding to the initial setting. Then, the direction setting unit 110 makes the end part 10 transmit ultrasound waves via the transmitter unit 105 towards around the transmission direction of the initial setting, for example, in directions adjacent to the transmission direction of the initial setting.

<<Acquisition of Signal Strength Information>>

In the Doppler mode, the receiver unit 106 sequentially obtains Doppler signals transmitted in different directions. The Doppler signals are those obtained by the Doppler signal processing unit 108, and derived from blood flow (if the observation object is blood flow: blood flow PWD or CWD), or derived from tissues (if the observation object is tissues: tissue Doppler imaging-PWD). In the following, unless otherwise noted, the observation object is described as blood flow. In this case, it is assumed that a signal derived from blood flow, from which components derived from tissues that represent noise are removed, is extracted as a Doppler signal. The Doppler signal processing unit 108 sends a Doppler signal to the search unit 111. Together with information on the transmission direction of ultrasound waves, the search unit 111 stores Doppler signals obtained sequentially from the signal processor in a storage unit (not illustrated). From each of the stored Doppler signals transmitted in different directions, the search unit 111 acquires signal strength information that indicates the strength of the signal. The signal strength information is, for example, blood flow sensitivity information in the pulsed Doppler mode. In this case, the blood flow sensitivity information may be the amplitude value or the brightness value of a waveform depicted in a Doppler spectrum image. Each time the search unit 111 obtains a Doppler signal, the search unit 111 may acquire signal strength information from the Doppler signal. In this case, the search unit 111 stores, in the storage unit (not illustrated), signal strength information obtained sequentially and information on the transmission direction of ultrasound waves.

<<Comparison of Signal Strength>>

Besides, the search unit 111 compares Doppler signals in different directions corresponding to, for example, predetermined cardiac time phase, and obtains a Doppler signal having a higher signal strength. By the comparison of signal strength, a Doppler signal indicating the highest signal strength is stored together with information on the corresponding transmission direction of ultrasound waves. The search unit 111 may acquire the signal strength upon acquisition of each Doppler signal. The search unit 111 may also be configured to obtain the highest signal strength from Doppler signals at each time point, after the completion of the search process described below.

<<End of Search>>

The transmission of ultrasound waves and the process of acquiring Doppler signals corresponding thereto continue, under the control of the direction setting unit 110, until a predetermined condition is satisfied. Examples of the predetermined condition include completion of predetermined times of transmission, completion of transmission in a predetermined range (a predetermined angle range from the sound source), elapse of a predetermined time, and the like. One predetermined condition corresponds to one cycle. Upon receipt of a Doppler signal obtained last in a cycle, the search unit 111 obtains signal strength information determining that it is the end of the cycle. Then, the search unit 111 compares Doppler signals with a Doppler signal having the highest signal strength in an earlier cycle. With this comparison, the search unit 111 completes one cycle of the search process, and determines information on the transmission direction of ultrasound waves corresponding to a Doppler signal having the highest signal strength. The search unit 111 transmits the information on the transmission direction of ultrasound waves thus determined to the direction setting unit 110.

<<Update of Direction Setting>>

The direction setting unit 110 compares the information on the transmission direction of ultrasound waves received from the search unit 111 to the transmission direction of ultrasound waves before the search process. If there is a difference between them, based on the information on the transmission direction of ultrasound waves received from the search unit 111, the direction setting unit 110 updates the setting of the transmission direction of ultrasound waves. In addition, based on the updated setting, the direction setting unit 110 changes the transmission direction of ultrasound waves to a new direction through the transmitter 141 of the end part 10, or the direction controller 16 and the drive unit 18. The direction setting unit 110 and the search unit 111 of this embodiment correspond to an example of a "controller".

The above is an example of the search process by the search unit 111. As an another example, when the continuous wave Doppler mode is initially selected by the operator, the signal strength of a Doppler signal may be obtained in response to the start of the transmission of ultrasound waves without waiting for the elapse of a predetermined time as described above. In this case, changes in signal strength in the same transmission direction may be continuously obtained based on Doppler signals acquired sequentially. However, in the continuous wave Doppler mode, ultrasound waves are continuously transmitted and received. Therefore, it is preferable to search the transmission direction of ultrasound waves as well as changing the transmission direction also at predetermined time intervals, in the same manner as the search of the transmission direction based on the signal strength as described above.

Due to the breathing, beats, body movement, throat reflection, emetic response, and the like of the subject, the transmission direction of ultrasound waves sometimes shifts from the object observed by the ultrasound diagnosis apparatus. In particular, if the observation object shifts not in the depth direction in the transmission direction of ultrasound waves, but in a direction deviating from the direction (orthogonal direction, etc.), it is difficult to continue the monitoring by the ultrasound diagnosis apparatus. Thus, each time a shift occurs, it is required to adjust the rotation and tilt of the ultrasound transducer 12 of the end part 10, the focus and transmission direction of ultrasound beams, and the like. Alternatively, each time a shift occurs, it is required to adjust the sample volume location (depth).

PWD mode has a range resolution. For example, during monitoring in the PWD mode, as well as the adjustment of the transmission direction of ultrasound beams, the sample volume location (depth) is adjusted with respect to the distance direction in the sound ray (scan line) of the ultrasound beams.

On the other hand, CWD mode has no range resolution. For example, during monitoring in the CWD mode, adjustment is performed for obtaining a location (depth) where the signal strength of a Doppler signal is the highest while the focus position (depth) of ultrasound beams is being changed.

However, it may be a heavy burden for the operator to keep monitoring shifts and also adjust them. If the operator bears these tasks, it may cause a decrease in the efficiency of monitoring inside the subject's body by the ultrasound diagnosis apparatus. In the case of long-term monitoring, if the operator bears the tasks, since it is difficult for the operator to keep monitoring whether the transmission direction of ultrasound waves is appropriate, it may interfere with the implementation of the monitoring. In this respect, the ultrasound diagnosis apparatus 100 includes the search unit 111 as described above to periodically adjust the transmission direction of ultrasound waves, thus solving the problems. That is, the ultrasound diagnosis apparatus 100 including the search unit 111 can improve the operation efficiency without imposing burdensome tasks on the operator in monitoring inside the subject's body. Moreover, the ultrasound diagnosis apparatus 100 including the search unit 111 can effectively cope with long-term monitoring.

(Biological Information Measuring Unit)

In FIG. 5, the biological information measuring unit 120 is connected to the main body 101. The biological information measuring unit 120 generates information indicating the conditions of the subject such as a biological signal, and sends the generated information to the main body 101. Examples of the biological information measuring unit 120 include bioelectric equipment (electrocardiograph, electroencephalograph, electromyography, etc.), respiratory equipment (respiratory flow meters, electronic spirometers, respiratory resistance meters, etc.), and medical monitoring equipment (singular monitor (bedside monitor), multiple monitors (central monitor), etc.), and the like. The medical monitoring equipment is configured to monitor vital signs such as ECG, blood pressure, respiratory rate, body temperature, pulse rate, blood oxygen saturation, exhaled gas partial pressure, and the like.

For example, if the biological information measuring unit 120 is an electrocardiograph, the main control unit 104 receives ECG waveform from the biological information measuring unit 120 via the receiver unit 106 and the like. Although FIG. 5 illustrates the biological information measuring unit 120 that is located outside the main body 101, some part thereof may be arranged in the main body 101 so that the measurement is performed in the main body 101.

<Operation>

Figure 9:
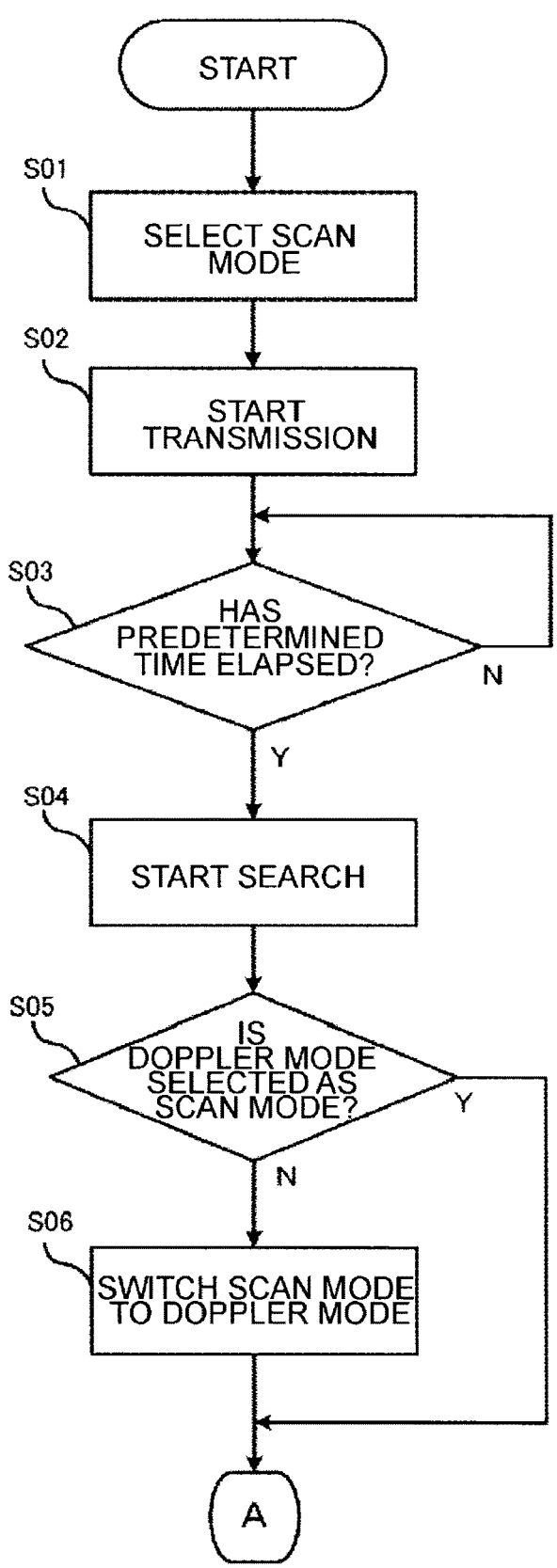
FIG. 9 is a flowchart schematically illustrating the operation of the ultrasound diagnosis apparatus of the first embodiment.
Figure 10:
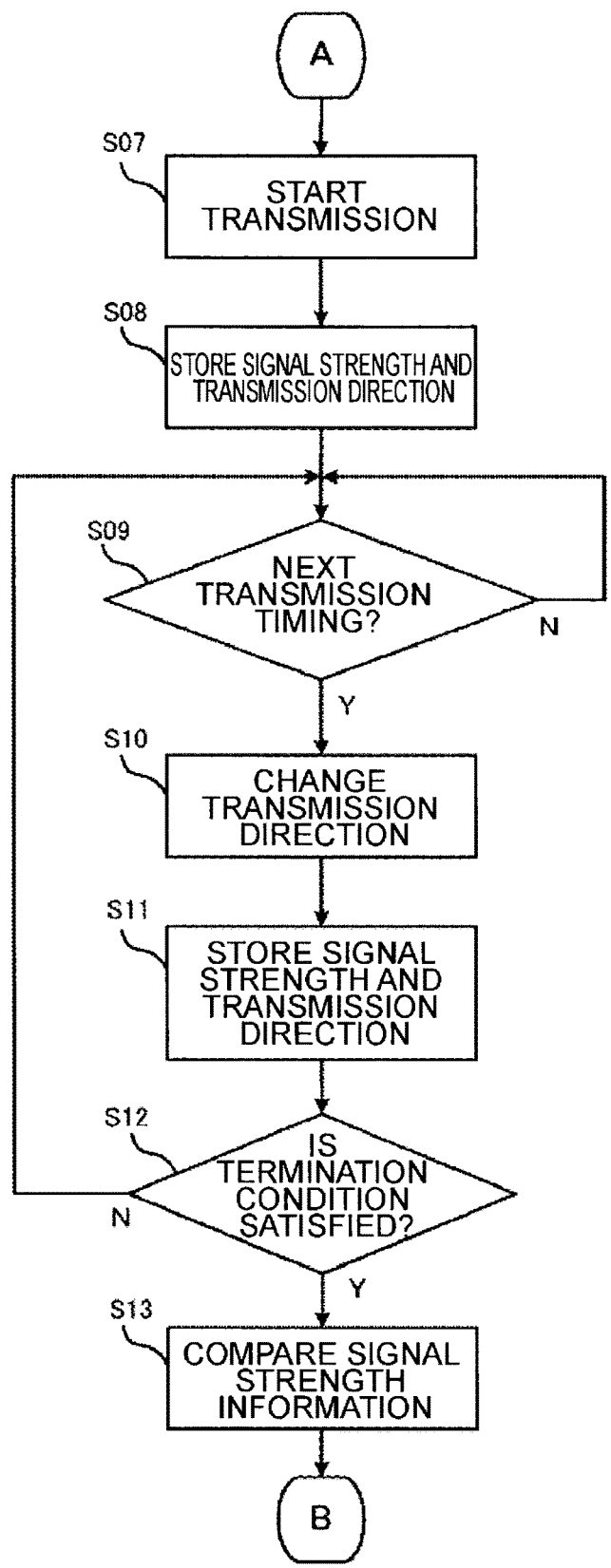
FIG. 10 is a flowchart schematically illustrating the operation of the ultrasound diagnosis apparatus of the first embodiment.
Figure 11:
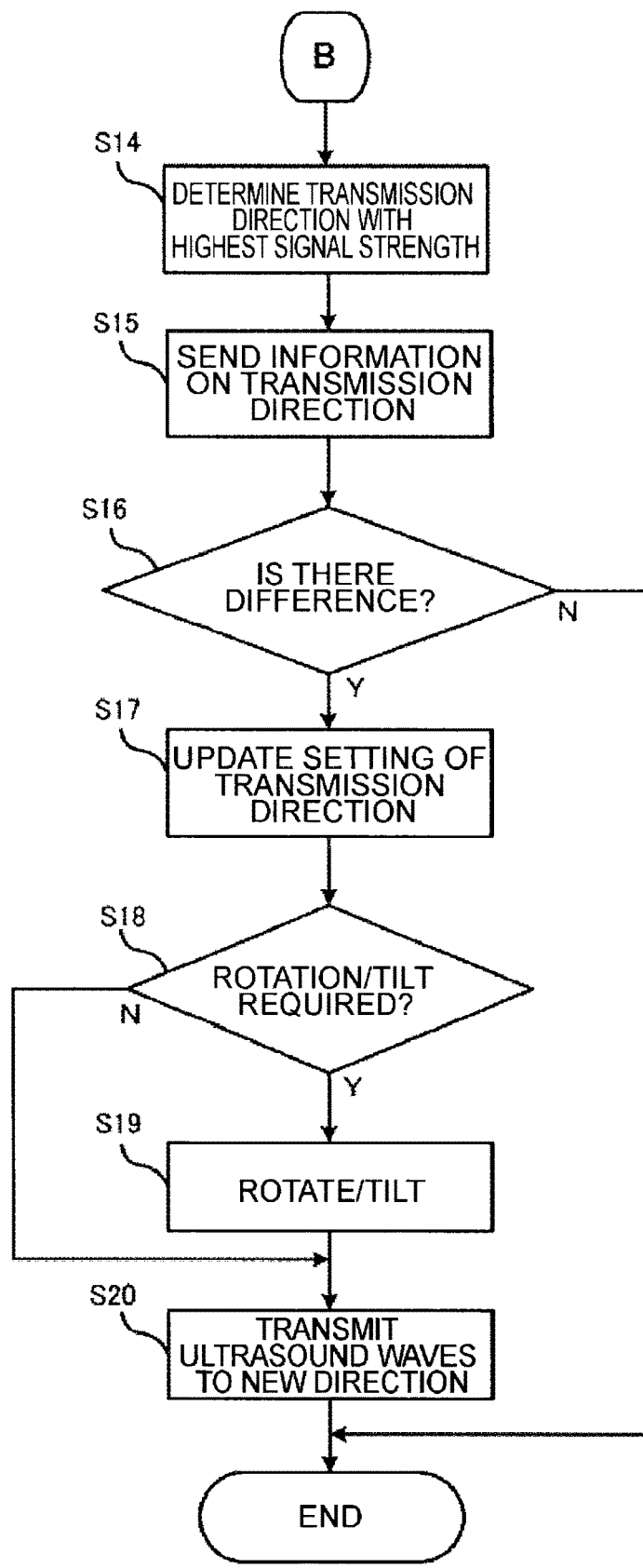
FIG. 11 is a flowchart schematically illustrating the operation of the ultrasound diagnosis apparatus of the first embodiment.

In the following, a description is given of a control flow to perform the search process at predetermined time intervals as well as displaying a B-mode image, a Doppler spectrum image, and ECG waveform in parallel according to the embodiment with reference to FIGS. 9 to 11. FIGS. 9 to 11 are flowcharts schematically illustrating the operation of the ultrasound diagnosis apparatus 100 of the first embodiment.

(Step S01)

The operator selects a scan mode and determines the initial setting (transmission direction, transmission focal point, receive focal point, sample volume setting, etc.) using the operation unit 102. Through the transmitter unit 105 of the main body 101 and the I/F 15 of the end part 10, the main control unit 104 sends the transmit-receive controller 14 of the end part 10 a control signal related to the drive control of the ultrasound transducer 12 according to the scan mode. At this time, the main control unit 104 may be configured to obtain ECG waveform from the biological information measuring unit 120 via the receiver unit 106 or the like. In addition, the display unit 103 may display the ECG waveform.

(Step S02)

In one example, the transmit-receive controller 14 generates a transmission drive pulse at the timing based on the rate pulse that is delayed by the transmission waveform generator 141*b*. The transmission drive pulse is amplified by the transmitter amplifier 141*c*, and sent to the switching unit 143. With this, predetermined ones of the ultrasound oscillators 12*a* are driven. Thus, the ultrasound transducer 12 emits predetermined ultrasound waves. In this way, the transmission of ultrasound waves is started. When the scan mode is the B mode, the receiver unit 106 sends an echo signal received from the end part 10 to the B-mode signal processing unit 107. The B-mode signal processing unit 107 performs signal processing thereon, thus generating RAW data. The generating unit 109 generates a B-mode image based on the RAW data. The display unit 103 displays the B-mode image as appropriate.

(Step S03)

The main control unit 104 determines whether a predetermined time has elapsed from the start of the transmission of ultrasound waves based on the selected scan mode. If, in step S03, determining that the predetermined time (e.g., any time period set by the operator) has not elapsed (Step S03; No), the main control unit 104 repeats this determination.

(Step S04)

In step S03, having determined that the predetermined time has elapsed (step S03; Yes), the main control unit 104 makes the end part 10 start transmitting/receiving ultrasound waves via the transmitter unit 105 for the search process. If a B-mode image BI is displayed on the display unit 103 (see FIG. 6), the main control unit 104 may prompt the operator to specify the position of sample volume to obtain a Doppler signal. The operator specifies any region of the B-mode image as sample volume using the operation unit 102. As for the direction of the sample volume, in FIG. 6, the transmission direction is indicated by a broken line L1 extending from the left atrium LA through the mitral valve M to the left chamber and passing by the center of the left heart. The depth of the sample volume (sampling gate) in the case of PW Doppler is, for example, set as a position on the broken line L1 that does not intersect the mitral valve in the left ventricular cavity. The specified depth and direction of the sample volume are sent to the direction setting unit 110, and the direction setting unit 110 returns information on the transmission direction of ultrasound waves from the sound source via the transmitter unit 105. The position of the sample volume may be specified prior to step S04.

(Step S05)

The main control unit 104 determines whether the Doppler mode is selected as scan mode in step S01. If it is determined that the scan mode is the Doppler mode (step S05; Yes), the process proceeds to step S07.

(Step S06)

In step S05, if it is determined that the scan mode is not the Doppler mode (step S05; No), the main control unit 104 switches the scan mode to the Doppler mode to start the search process.

(Step S07)

For the search process, the main control unit 104 makes the end part 10 start transmitting ultrasound waves in the Doppler mode via the transmitter unit 105. If a scan mode other than the Doppler mode (B-mode, etc.) is selected in step S01, after the Doppler mode transmission, the scan mode is switched alternately between the Doppler mode and the scan mode selected in step S01.

(Step S08)

The receiver unit 106 receives an echo signal based on the Doppler mode from the end part 10. The Doppler signal processing unit 108 performs the signal processing on the echo signal to obtain a Doppler signal and sends the Doppler signal to the search unit 111. The search unit 111 generates signal strength information based on the Doppler signal in the time corresponding to predetermined cardiac time phase. The signal strength information generated by the search unit 111 is stored in the storage unit (not illustrated) with the information on the transmission direction of ultrasound waves.

(Step S09)

Based on the ECG waveform fed from the biological information measuring unit 120, the main control unit 104 measures the timing of the next transmission of ultrasound waves in the search process. The main control unit 104 repeats this (step S09; No) until the timing of the next transmission of ultrasound waves.

(Step S10)

In step S09, having determined that it is the timing of the next transmission of ultrasound waves based on the ECG waveform (step S09; Yes), the main control unit 104 controls the direction setting unit 110 so that the end part 10 transmits ultrasound waves after changing the transmission direction of ultrasound waves from the direction initially set to a direction around it. If the scan mode in the initial setting is not the Doppler mode, the main control unit 104 changes the transmission direction of ultrasound waves at the end part 10 after switching the scan mode to the Doppler mode.

(Step S11)

Having received an echo signal related to ultrasound waves transmitted by changing the transmission direction, the receiver unit 106 sends the signal to the Doppler signal processing unit 108. The search unit 111 generates signal strength information based on the Doppler signal received from the Doppler signal processing unit 108, and stores it in the storage unit (not illustrated) with the information on the transmission direction of ultrasound waves. The main control unit 104 obtains the predetermined cardiac time phase based on the ECG waveform fed from the biological information measuring unit 120. The main control unit 104 also obtains signal strength in the time corresponding to the predetermined cardiac time phase from among Doppler signals acquired successively.

(Step S12)

The main control unit 104 determines whether the termination condition of the search process, such as completion of predetermined times of transmission, completion of transmission in a predetermined range (a predetermined angle range from the sound source), elapse of a predetermined time, and the like, is satisfied. In step S12, having determined that the termination condition of the search process is not satisfied (step S12; No), the main control unit 104 repeats steps S09 to S12.

(Step S13)

In step S12, if the main control unit 104 determines that the termination condition of the search process is satisfied (Step S12; Yes), the search unit 111 retrieves pieces of the signal strength information from the storage unit (not illustrated) and compares them. The search unit 111 may be configured to compare signal strength information with prior one each time signal strength information is obtained through the repetition of steps S09 to S11. In this case, since the provisional highest signal strength has already been determined, the search unit 111 compares signal strength obtained most recently with the provisional highest signal strength at the previous time.

(Step S14)

According to the result of the comparison in step S13, the search unit 111 determines the transmission direction of ultrasound waves with the highest signal strength.

(Step S15)

The search unit 111 sends the direction setting unit 110 information on the transmission direction of ultrasound waves thus determined.

(Step S16)

Comparing the transmission direction set in advance with the information on the transmission direction received in step S15, the direction setting unit 110 determines whether there is a difference between them.

(Step S17)

In step S16, having determined that there is a difference between the transmission direction set in advance and the information on the transmission direction received in step S15 (step S16; Yes), the direction setting unit 110 updates the setting of the transmission direction of ultrasound waves based on the information on the transmission direction of ultrasound waves received in step S15.

(Step S18)

The direction setting unit 110 determines whether the ultrasound transducer 12 is required to be rotated or tilted by the direction controller 16 and the drive unit 18 based on the updated setting.

(Step S19)

In step S18, having determined that the ultrasound transducer 12 is required to be rotated or tilted (step S18; Yes), the direction setting unit 110 rotates or tilts the ultrasound transducer 12 with the direction controller 16 and the drive unit 18. However, when the 2D array ultrasound transducer 12 is used, there may be a case where this determination is not necessary.

(Step S20)

The direction setting unit 110 changes the transmission direction of ultrasound waves to a new direction and transmits ultrasound waves through the transmitter 141 of the end part 10. In step S18, having determined that the ultrasound transducer 12 is not required to be rotated or tilted (step S18; No), the direction setting unit 110 performs step S20 without performing step S19.

In step S16, having determined that there is no difference between the transmission direction set in advance and the information on the transmission direction received in step S15 (step S16; No), the direction setting unit 110 ends the process without performing steps S17 to S20.

The ultrasound diagnosis apparatus 100 of this embodiment transmits ultrasound waves at predetermined intervals in the transmission direction set in advance and directions around it, and acquires a plurality of Doppler signals corresponding to different transmission directions. The search unit 111 compares pieces of information on the signal strength of the Doppler signals corresponding to the different transmission directions, thereby determining the transmission direction of ultrasound waves with the highest signal strength. The direction setting unit 110 changes the transmission direction of ultrasound waves at the end part 10 to the transmission direction. Thus, even if the end part 10 shifts in the subject's body due to the breathing, beats, body movement, throat reflection, emetic response, and the like of the subject, and the transmission direction of ultrasound waves shifts from the object to be observed, the ultrasound diagnosis apparatus 100 can change the transmission direction of ultrasound waves to follow the shift, thereby enabling the continuation of monitoring inside the subject' body without imposing burdensome tasks on the operator. Moreover, even in long-term monitoring, the ultrasound diagnosis apparatus 100 can avoid a decrease in the operation efficiency.

The ultrasound diagnosis apparatus 100 of this embodiment includes the end part 10. The end part 10 includes, for example, the ultrasound transducer 12 in the container 10a in a capsule form. The end part 10 is inserted in the subject's body. On the other hand, if a common transesophageal echocardiography (TEE) probe is inserted in the esophagus, the guide tube portion form the grip to the end part stays in the esophagus. For example, when ultrasound waves are transmitted and received between a predetermined position in the esophagus and the heart, the guide tube portion is placed in the esophagus while at least ultrasound waves are being transmitted and received. That is, while an observation site such as the heart or the like is being monitored, the guide tube portion to the end part stays in the esophagus of the subject all the time.

The guide tube portion and the end part of the TEE probe are provided therein with not only a signal line for exchanging signals with the ultrasound transducer and a power supply line or the like for supplying power, but also a wire for bending the end part. This means that the subject is obliged to bear with patience the guide tube portion or the like that includes therein a wire and the like being placed in the esophagus. If the monitoring continues for a long time, it may impose a burden on the subject depending on his/her condition. As a result, the TEE probe may not be used for the continuous monitoring of the observation site. If ultrasound waves are transmitted and received at the outside of the body to avoid this problem, it is required to consider the influence of tissues (bones, lungs, etc.) present in the way to the observation site from the outside. As in the embodiment, if the end part 10 is in a capsule form, and only minimal lines such as a signal line and a power supply line are passed through the cable 11, it is possible to reduce the burden on the subject compared to the case of using the TEE probe. Further, with the use of the cylindrical support having a hollow penetrating along the central axis, even if the end part 10 is placed at a fixed position for a long time, the esophagus can maintain its functions.

<Modification 1>

Figure 12A:
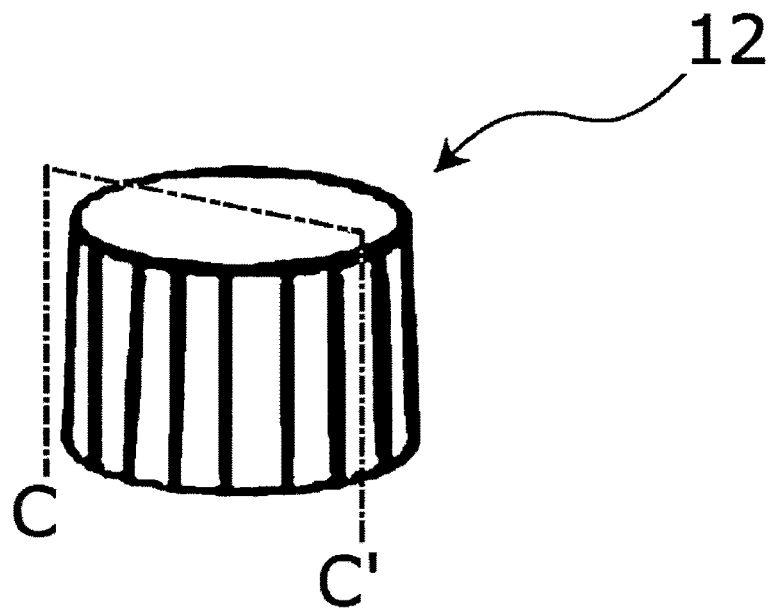
FIG. 12A is a schematic perspective view of an ultrasound transducer according to a modification of the first embodiment.
Figure 12B:
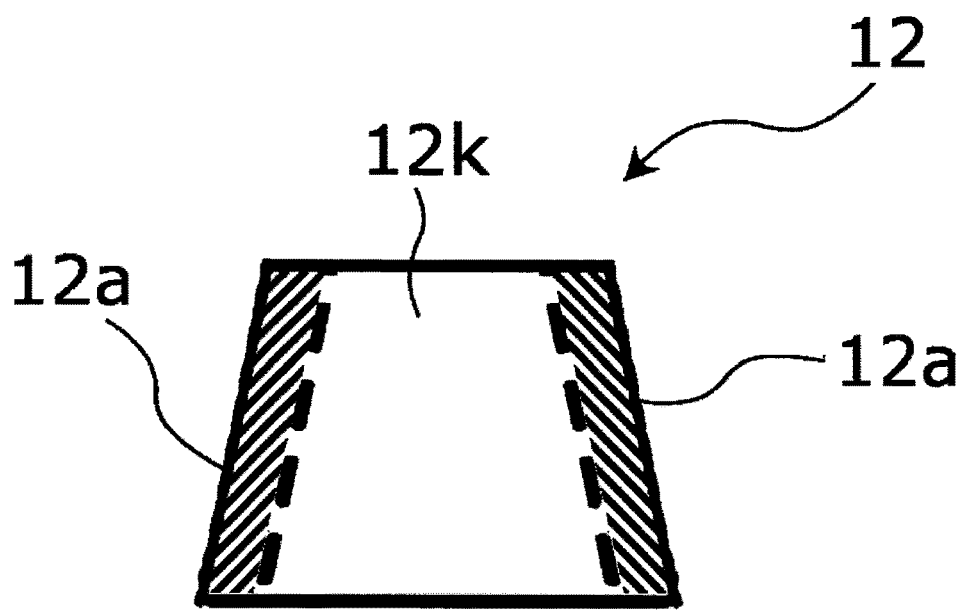
FIG. 12B is a schematic cross section taken along line C-C' in FIG. 12A.

In the following, a modification 1 of the first embodiment is described with reference to FIGS. 12A and 12B. FIG. 12A is a schematic perspective view of the ultrasound transducer 12 according to the modification 1 of the first embodiment. FIG. 12B is a schematic cross section taken along line C-C' in FIG. 12A. As illustrated in FIGS. 12A and 12B, the ultrasound transducer 12 of the modification 1 is provided with a support 12k for the ultrasound oscillators 12a, the diameter of which increases gradually from one end face toward the other in the axial direction so that the shape is flared at the bottom.

In this structure, the ultrasound oscillators 12a are arranged to be tilted with respect to the longitudinal axis of the container 10a (the axis in the direction in which the end part 10 is inserted). Thus, the ultrasound transducer 12 need not be tilted by the actuator or the like differently from the above embodiment. For example, even if the heart is located in such a position where it looks up at the ultrasound wave radiation surface of the ultrasound transducer 12 of the end part 10 inserted around the middle of the esophagus, the heart can be included in ROI.

This eliminates the need of drive control by the drive unit 18, thereby enabling space-saving in the container 10a.

Further, if the transmission direction of ultrasound waves shifts from the observation object, the ultrasound diagnosis apparatus of the modification 1 can change the transmission direction of ultrasound waves to follow the shift of the end part 10, thereby enabling the continuation of monitoring inside the subject' body without imposing burdensome tasks on the operator.

<Modification 2>

Next, a modification 2 of the first embodiment is described. In this modification, the transmitter unit 105 and the receiver unit 106 of the main body 101 implement the most functions of the transmitter 141 and the receiver 142 of the end part 10 of the first embodiment. With this, the internal structure of the container 10a may be simplified. Described below is an example of the functions of the transmitter unit 105 and the receiver unit 106.

(Transmitter Unit—Modification 2)

The transmitter unit 105 of the main body 101 includes a clock generation circuit, a transmitter delay circuit, and a pulser circuit (not illustrated). The main control unit 104 controls the clock generation circuit, the transmitter delay circuit, the pulser circuit, and the like. The clock generation circuit generates clock signals for determining the transmission frequency and the transmission timing of ultrasound waves. For example, the clock generation circuit feeds the transmitter delay circuit with a reference clock signal. The transmitter delay circuit sends the pulser circuit a drive signal having a predetermined delay time. The predetermined delay time is determined based on the transmission focal point of ultrasound waves. The pulser circuit includes therein as many pulsers as individual channels corresponding to the ultrasound oscillators 12a, and generates transmission drive pulses.

The pulser circuit repeatedly generates a rate pulse to form transmission ultrasound waves at a predetermined repetition frequency (PRF). The transmitter delay circuit provides the rate pulse with a transmission delay time related to the transmission direction and the transmission focus. Transmission drive pulses are generated at timing based on the rate pulses each being delayed. The transmission drive pulses are sent to the end part 10 through the cable 11, and fed to the ultrasound oscillators 12a of the ultrasound transducer 12 via the transmit-receive controller 14. The transmission drive pulses excite the piezoelectric elements. As described above, the transmitter delay circuit provides the rate pulse with a transmission delay time to focus ultrasound waves for transmission, thereby converging the ultrasound waves into a beam. With this, the transmission directivity of the ultrasound waves is determined. In addition, the transmitter delay circuit changes the transmission delay time to be given to each rate pulse, thereby controlling the transmission direction of ultrasound waves from the ultrasound wave radiation surface.

(Receiver Unit—Modification 2)

The receiver unit 106 of the main body 101 is controlled by the main control unit 104. The receiver unit 106 of the main body 101 receives echo signals corresponding to ultrasound waves reflected from the subject. Having received the echo signals received by the end part 10, the receiver unit 106 performs delay addition processing on them. Thus, the receiver unit 106 converts the analog echo signals to digital data having been subjected to phasing (i.e., subjected to beam forming). Specific examples are as follows.

The receiver unit 106 includes, for example, a preamplifier circuit, an A/D converter, a receiver delay circuit, and an adder (all not illustrated). The preamplifier circuit amplifies echo signals received from the ultrasound transducer 12 with respect to each receiver channel. The A/D converter converts the amplified echo signals to digital signals. Having been converted into digital signals, the echo signals are each stored in a digital memory (not illustrated). The digital memory is provided for each channel (or each element). Each echo signal is stored in the corresponding digital memory. The echo signal is also stored in an address corresponding to the time it is received.

The receiver delay circuit provides echo signals converted to digital signals with a delay time required to determine the reception directivity. The reception delay time is calculated for each element. The adder adds up the echo signals having the delay time. The adder reads each of the echo signals from the digital memory as appropriate based on the required delay time calculated, and adds up them. The adder repeats this addition while changing a reception focus position along the transmission beam. The adder emphasizes a reflection component from a direction corresponding to the reception directivity. The received beam signal processed by the receiver unit 106 is sent to the signal processor (the B-mode signal processing unit 107, the Doppler signal processing unit 108).

[Second Embodiment]

In the following, the ultrasound diagnosis apparatus 100 according to the second embodiment is described. In the second embodiment, the operation of the search unit 111 is different from that of the first embodiment. The ultrasound diagnosis apparatus 100 of the second embodiment is similar to that of the first embodiment in other respects. The differences are mainly described below.

In the first embodiment, the search unit 111 is configured to determine the optimal transmission direction of ultrasound waves based on the signal strength of Doppler signals. On the other hand, in the ultrasound diagnosis apparatus 100 of the second embodiment, the search unit 111 performs the search process based on a waveform indicating blood flow information generated by the generating unit 109.

(Overview of Search Unit)

For example, the search unit 111 of the second embodiment may compare a waveform based on Doppler signals previously stored with a waveform based on Doppler signals obtained sequentially in the search process (e.g., FIG. 7A). Preferably, the waveforms of the Doppler signals are compared in each predetermined period (e.g., in one cardiac cycle) that is synchronized with cardiac time phase. As a result of the comparison, the search unit 111 may be configured to determine the transmission direction of ultrasound waves by obtaining a direction with the highest similarity to the waveform based on the Doppler signal stored in advance. In the first embodiment described above, an example is described in which the transmission direction is determined based on the signal strength of Doppler signals. Here, in the case of pulsed Doppler, if sample volume touches the myocardial tissue or the valve, received beam signals are saturated, which may cause a significant increase in the signal strength of Doppler signals as compared to the signals obtained from the blood stream. In case of this, preferably, the search unit 111 provides an upper limit to expected values of the signal strength of Doppler signals, and searches for a direction where the highest signal strength is obtained within the range of the expected values. Further, as described below, by searching for a direction with the highest similarity of Doppler waveforms in a predetermined period, the search unit 111 can estimate a transmission direction with high accuracy while reducing the effect of saturation. Hereinafter, the waveform based on Doppler signals previously stored (reference waveform) may be sometimes referred to as "second waveform". Besides, the waveform based on Doppler signals obtained sequentially in the search process may be sometimes referred to as "first waveform". The second waveform corresponds to an example of "second waveform pattern". The first waveform corresponds to an example of "first waveform pattern".

<<Generation of Reference Waveform Data>>

The second waveform data related to the second waveform is stored in the storage unit (not illustrated). The second waveform is compared with the first waveform in the search process. The second waveform data is acquired until a predetermined time has elapsed from the start of transmitting/receiving of ultrasound waves based on, for example, acquisition conditions determined in advance in selected scan mode. In this case, if the scan mode selected by the operator is the B mode, the main control unit 104 controls the end part 10, through the transmitter unit 105, to alternately switch between the control of electronic scanning of the ultrasound transducer 12 according to the B-mode and the control of ultrasound wave transmitting/receiving according to the Doppler mode. The control switching is repeated until a predetermined time has elapsed. At this time, the transmission direction of ultrasound waves in the Doppler mode is a direction set in advance as the initial setting. The initial setting is determined by the operator at the start timing of the transmission of ultrasound waves, or before or after it. In the generation of the second waveform, unlike the search process, ultrasound waves are transmitted in a set direction without a change in the transmit direction.

The main control unit 104 also controls the transmit-receive controller 14 of the end part 10 to acquire Doppler signals in predetermined cardiac time phase (diastole phase, etc.) for generating the second waveform data. For this control, the main control unit 104 obtains ECG waveform from the biological information measuring unit 120. The generating unit 109 generates an image (Doppler spectrum image, etc.) indicating waveform in the Doppler mode based on the Doppler signals.

The search unit 111 extracts a waveform corresponding to the predetermined cardiac time phase in the ECG waveform from the image indicating waveform in the Doppler mode. The search unit 111 generates the second waveform based on the waveform, and stores it in the storage unit. Data indicating a waveform obtained in advance may be stored as the second waveform data without the above process of generating the second waveform data. For example, it may also be possible to use waveform data indicating a typical waveform according to the condition of the subject. For another example, the search unit 111 may extract a specific waveform from waveforms based on Doppler signals acquired from the same subject in the past by referring to the current condition of the subject, and use the specific waveform as the second waveform.

<<Start of Search>>

The transmitter unit 105 of the main body 101 starts transmitting ultrasound waves in the Doppler mode to obtain the first waveform used in the search process of the search unit 111. Triggered by the elapse of a predetermined time from when the second waveform is acquired, the transmitter unit 105 makes the end part 10 transmit ultrasound waves in the Doppler mode. The time interval at which the search process is performed can be set arbitrarily.

<<Ultrasonic Transmission Based on ECG Waveform>>

In the search process, the time interval, at which ultrasound waves are transmitted while the transmission direction is changed, is set correspondingly to cardiac time phase in the second waveform. For example, the main control unit 104 receives ECG waveform from the biological information measuring unit 120. Next, the main control unit 104 obtains cardiac time phase corresponding to cardiac time phase (diastole phase, etc.) in the second waveform from the ECG waveform. The main control unit 104 then sends a control signal on the transmission timing of ultrasound waves to the transmitter unit 105 based on the cardiac time phase. The main control unit 104 may not necessarily be configured to send a control signal on the transmission timing of ultrasound waves in predetermined cardiac time phase. For another example, the main control unit 104 may be configured to obtain predetermined cardiac time phase from the ECG waveform fed by the biological information measuring unit 120, and generate the first waveform (described later) corresponding to the predetermined cardiac time phase among Doppler signals acquired sequentially.

<<Generation of Waveform Image>>

The Doppler signal processing unit 108 performs the same signal processing as in the first embodiment on echo signals received from the receiver unit 106, thereby sending RAW data of the Doppler mode to the generating unit 109. The generating unit 109 sequentially generates Doppler spectrum images based on the RAW data.

<<Generation of First Waveform>>

At this time, the main control unit 104 obtains cardiac time phase corresponding to that of the second waveform from the ECG waveform fed by the biological information measuring unit 120, and send it to the search unit 111. The search unit 111 extracts a waveform in the cardiac time phase corresponding to that in the second waveform from the Doppler spectrum image generated by the generating unit 109. The search unit 111 sequentially generates such waveform for each of transmission directions as the first waveform.

<<Calculation of Similarity of Waveforms>>

The search unit 111 determines the similarity between the second waveform stored and each of the first waveforms generated sequentially in the search process. The similarity can be obtained by, for example, cross-correlation operation. Based on the cross-correlation coefficient value between the first waveform and the second waveform, the search unit 111 determines the similarity of the two waveforms. The similarity thus obtained is stored in the storage unit (not illustrated) with information on the transmission direction of ultrasound waves.

<<Comparison of Similarity>>

Comparing the first waveforms in different directions, the search unit 111 determines one which is more similar to the second waveform. The first waveform with the highest similarity in the comparison is stored with information on the corresponding transmission direction of ultrasound waves. The first waveform with the highest similarity corresponds to an example of a "similar waveform pattern".

Figure 13:
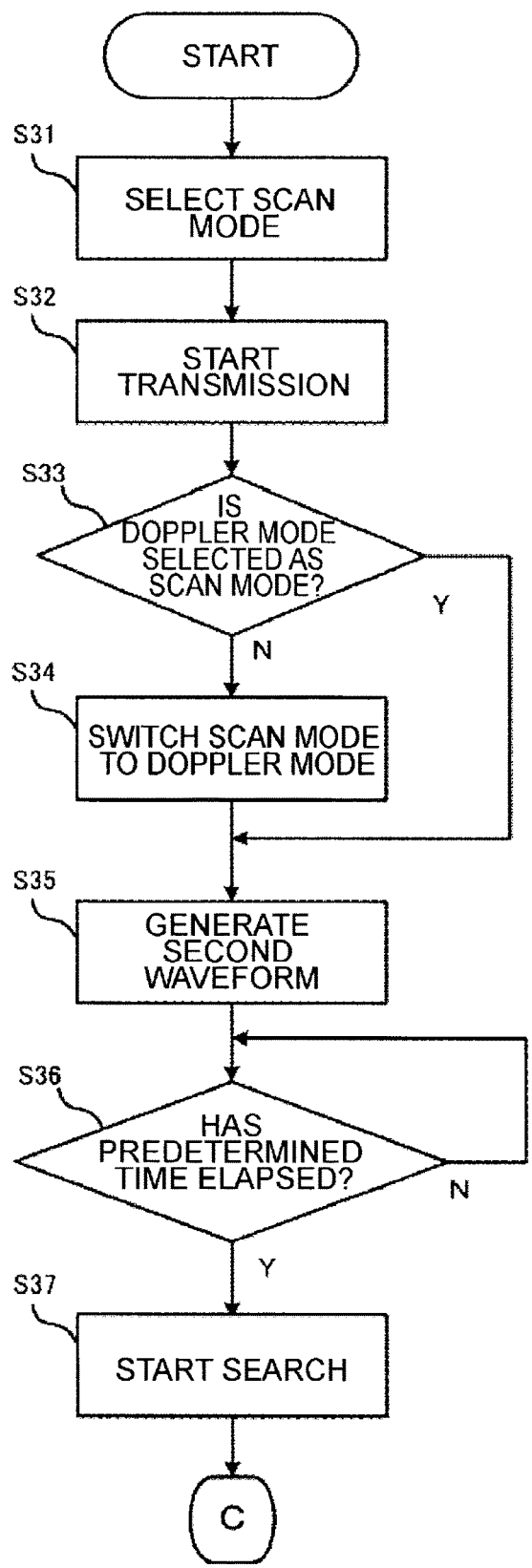
FIG. 13 is a flowchart schematically illustrating the operation of an ultrasound diagnosis apparatus according to a second embodiment.
Figure 14:
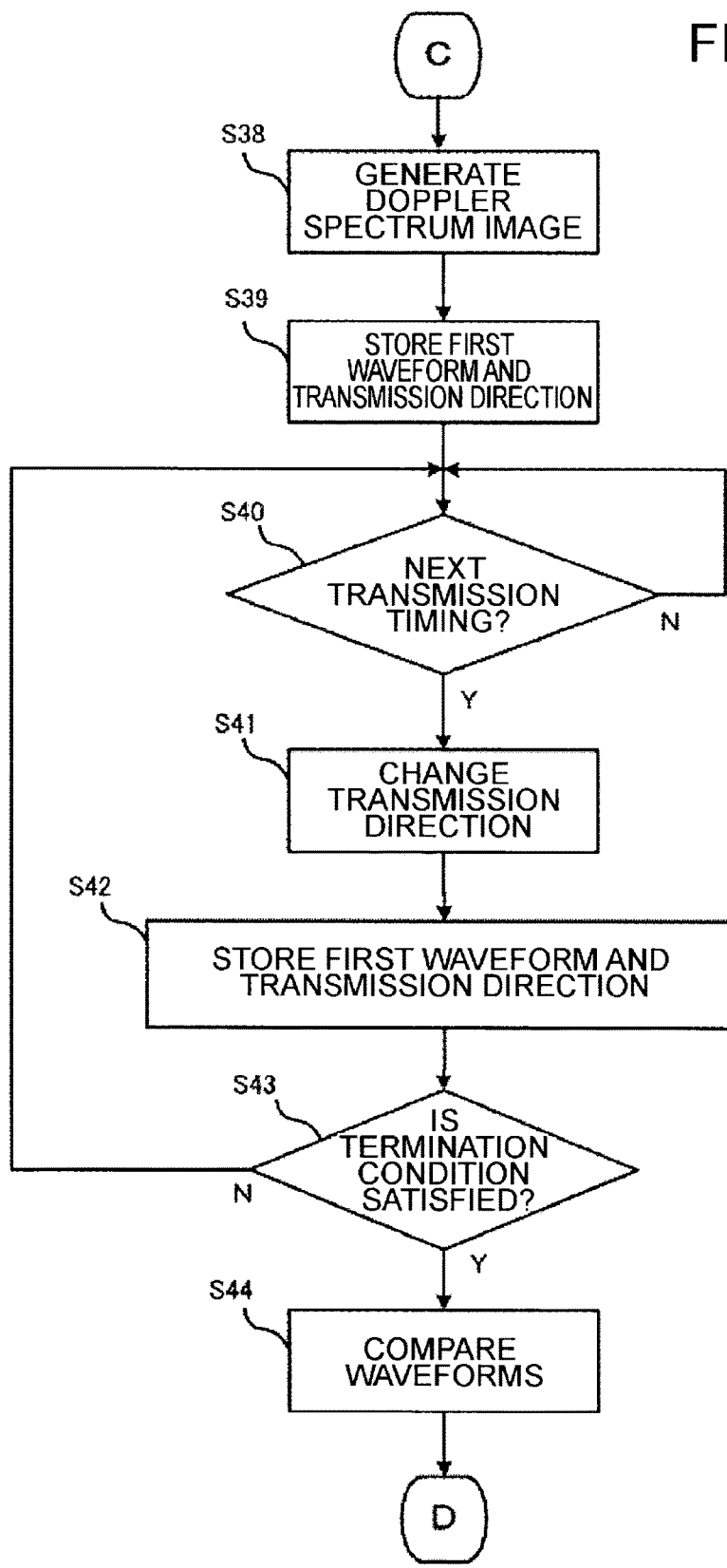
FIG. 14 is a flowchart schematically illustrating the operation of the ultrasound diagnosis apparatus of the second embodiment.
Figure 15:
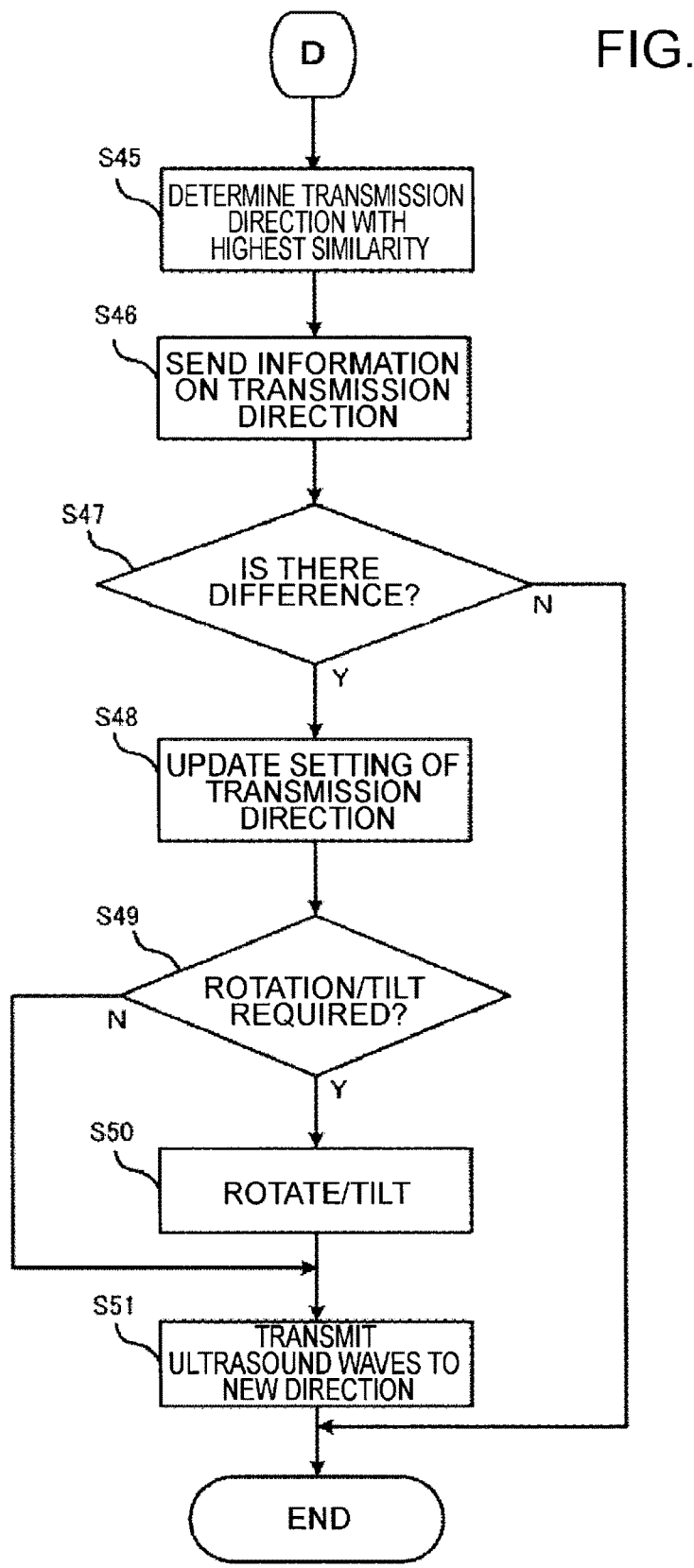
FIG. 15 is a flowchart schematically illustrating the operation of the ultrasound diagnosis apparatus of the second embodiment.

In the following, a description is given of a control flow to perform the search process at predetermined time intervals as well as displaying a Doppler spectrum image and ECG waveform in parallel according to the embodiment with reference to FIGS. 13 to 15. FIGS. 13 to 15 are flowcharts schematically illustrating the operation of the ultrasound diagnosis apparatus 100 of the second embodiment.

Incidentally, with the parallel display of a Doppler spectrum image and ECG waveform, monitoring is conducted on, for example, the peak value of the left ventricular inflow in systole as illustrated in FIG. 7B. At this time, the ECG waveform is acquired, and thus cardiac time phase for Doppler waveform can be identified (diastole, systole, etc.). When, as illustrated in FIG. 7B, the left ventricular inflow that occurs during diastole is monitored, the polarity of a waveform indicating the direction of blood flow is detected as negative (lower side in FIG. 7B). On the other hand, as illustrated in FIG. 7B, if the polar component of a reverse waveform (forward direction (upper side in FIG. 7B)) is detected in systole, it means that there exists mitral regurgitation (MR in FIG. 7B). However, if the presence of mitral regurgitation MR is determined only by the polarity of a waveform, this determination may result in error. This is because when the end part 10 shifts with respect to the left ventricular inflow (object to be observed), the transmission direction of ultrasound waves shifts. Thus, Doppler signals for the aortic ejection blood flow having the same positive polarity (upper side in FIG. 7B) are received in systole, and the waveform of the Doppler signals may be detected erroneously as mitral regurgitation MR. To avoid such erroneous detection, it is important that the search unit 111 performs the search process in consideration of cardiac time phase in monitoring.

(Step S31)

The operator selects a scan mode and determines the initial setting (transmission direction, transmission focal point, receive focal point, sample volume setting, etc.) using the operation unit 102. Through the transmitter unit 105 of the main body 101 and the I/F 15 of the end part 10, the main control unit 104 sends the transmit-receive controller 14 of the end part 10 a control signal related to the drive control of the ultrasound transducer 12 according to the scan mode. The main control unit 104 may be configured to obtain ECG waveform at this time from the biological information measuring unit 120 via the receiver unit 106 or the like. In addition, the display unit 103 may display the ECG waveform (e.g., FIG. 7).

(Step S32)

The ultrasound oscillators 12*a* are driven by the transmit-receive controller 14, thereby emitting predetermined ultrasound waves. In this way, the transmission of ultrasound waves is started. When the scan mode is the Doppler mode, the receiver unit 106 sends an echo signal received from the end part 10 to the Doppler signal processing unit 108. The Doppler signal processing unit 108 performs signal processing thereon, thus generating RAW data. The generating unit 109 generates a Doppler spectrum image based on the RAW data. The display unit 103 displays the Doppler spectrum image as appropriate.

(Step S33)

The main control unit 104 determines whether the Doppler mode is selected as scan mode in step S31. If it is determined that the scan mode is the Doppler mode (step S33; Yes), the process proceeds to step S35.

(Step S34)

In step S05, if it is determined that the scan mode is not the Doppler mode (step S33; No), the main control unit 104 switches the scan mode to the Doppler mode to start the search process.

(Step S35)

For the search process, the main control unit 104 makes the end part 10 start transmitting ultrasound waves in the Doppler mode via the transmitter unit 105. Via the receiver unit 106, an echo signal is sent from the end part 10 to the main body 101. The Doppler signal processing unit 108 performs the signal processing on the echo signal. Having received RAW data from the Doppler signal processing unit 108, the generating unit generates a Doppler spectrum image. The search unit 111 extracts a waveform corresponding to predetermined cardiac time phase in ECG waveform from the Doppler spectrum image. The search unit 111 generates the second waveform based on the waveform, and stores it in the storage unit.
(Step S36)

The main control unit 104 determines whether a predetermined time has elapsed from the start of the transmission of ultrasound waves based on the selected scan mode, or from when the second waveform is generated. If, in step S36, determining that the predetermined time has not elapsed (step S36; No), the main control unit 104 repeats this determination.
(Step S37)

In step S37, having determined that the predetermined time has elapsed (step S36; Yes), the main control unit 104 makes the end part 10 start transmitting/receiving ultrasound waves for the search process via the transmitter unit 105. If the scan mode selected in step S31 is not the Doppler mode, the main control unit 104 switches the scan mode to the Doppler mode to start the search process.
(Step S38)

The receiver unit 106 receives an echo signal based on the Doppler mode from the end part 10. The Doppler signal processing unit 108 performs the signal processing on the echo signal to obtain a Doppler signal and sends the Doppler signal to the generating unit 109. The generating unit 109 generates a Doppler spectrum image.
(Step S39)

The search unit 111 extracts a waveform in cardiac time phase corresponding to that in the second waveform from the Doppler spectrum image generated by the generating unit 109. The search unit 111 generates the first waveform based on the waveform. The search unit 111 stores the first waveform in the storage unit (not illustrated) with information on the transmission direction of ultrasound waves.
(Step S40)

Based on ECG waveform fed from the biological information measuring unit 120, the main control unit 104 measures the timing of the next transmission of ultrasound waves in the search process. The main control unit 104 repeats this (step S40 No) until the timing of the next transmission of ultrasound waves.
(Step S41)

In step S40, having determined that it is the timing of the next transmission of ultrasound waves based on the ECG waveform (step S40; Yes), the main control unit 104 controls the direction setting unit 110 so that the end part 10 transmits ultrasound waves after changing the transmission direction of ultrasound waves from the direction initially set to a direction around it. If the scan mode in the initial setting is not the Doppler mode, the main control unit 104 changes the transmission direction of ultrasound waves at the end part 10 after switching the scan mode to the Doppler mode.
(Step S42)

Having received an echo signal related to ultrasound waves transmitted by changing the transmission direction, the receiver unit 106 sends the signal to the Doppler signal processing unit 108. The generating unit 109 generates a Doppler spectrum image based on the Doppler signal processed by the Doppler signal processing unit 108. The search unit 111 extracts a waveform in cardiac time phase corresponding to that in the second waveform from the Doppler spectrum image generated by the generating unit 109. The search unit 111 generates the first waveform based on the waveform. The search unit 111 stores the first waveform in the storage unit (not illustrated) with information on the corresponding transmission direction of ultrasound waves.
(Step S43)

The main control unit 104 determines whether the termination condition of the search process, such as completion of predetermined times of transmission, completion of transmission in a predetermined range (a predetermined angle range from the sound source), elapse of a predetermined time, and the like, is satisfied. In step S43, having determined that the termination condition of the search process is not satisfied (step S43; No), the main control unit 104 repeats steps S40 to S43.
(Step S44)

In step S43, if the main control unit 104 determines that the termination condition of the search process is satisfied (Step S43; Yes), the search unit 111 retrieves the first waveforms from the storage unit (not illustrated) and compares them with the second waveform, thereby determining the similarity between the second waveform and each of the first waveforms (by the cross-correlation operation, etc.). In addition, the search unit 111 determines one with the highest similarity to the second waveform among the first waveforms.

The search unit 111 may be configured to compare the first waveform with the second waveform to determine the similarity between them each time the first waveform is generated through the repetition of steps S40 to S42. In this, the search unit 111 may also be configured to provisionally determine the first waveform with the highest similarity among similarities having been obtained in the past.

In this case, the search unit 111 compares the first waveform obtained most recently to that with the provisional highest similarity obtained at the previous time.
(Step S45)

According to the result of the comparison in step S44, the search unit 111 determines the transmission direction of ultrasound waves corresponding to the first waveform with the highest similarity.
(Step S46 to Step S50)

The following steps, i.e., sending information on the transmission direction (step S46), determining about a difference between the transmission directions (step S47), updating the setting of the transmission direction (step S48), determining necessity for rotating or tilting the ultrasound transducer 12 (step S49), rotating or tilting the ultrasound transducer 12 (step S50), and transmitting ultrasound waves in a new direction (step S51), are performed in the same manner as described in the first embodiment, and the details are not repeated here.

The ultrasound diagnosis apparatus 100 of this embodiment transmits ultrasound waves at predetermined intervals in the transmission direction set in advance and directions around it, and acquires a plurality of Doppler signals corresponding to different transmission directions. The search unit 111 compares each of a plurality of first waveforms corresponding to the different transmission directions with the second waveform (reference waveform) stored in advance, thereby determining the similarity to the second waveform. The search unit 111 determines the first waveform with the highest similarity among similarities thus obtained. The search unit 111 sends the transmission direction of ultrasound waves corresponding to the first waveform to the direction setting unit 110. The direction setting unit 110 changes the transmission direction of ultrasound waves to the transmission direction. Thus, even if the end part 10 shifts in the subject's body due to the breathing, beats, body movement, throat reflection, emetic response, and the like of the subject, and the transmission direction of ultrasound waves shifts from the object to be observed, the ultrasound diagnosis apparatus 100 can change the transmission direction of ultrasound waves to follow the shift, thereby enabling the continuation of monitoring inside the subject' body without imposing burdensome tasks on the operator. Moreover, even in long-term monitoring, the ultrasound diagnosis apparatus 100 can avoid a decrease in the operation efficiency.

As in the first embodiment, the ultrasound diagnosis apparatus 100 of the second embodiment may have the end part 10 in a capsule form. Moreover, the end part 10 may have a structure in which only minimal lines such as a signal line and a power supply line are passed through the cable 11. This makes it possible to reduce the burden on the subject compared to the case of using the TEE probe.

[Third Embodiment]

In the following, the ultrasound diagnosis apparatus 100 according to the third embodiment is described. In the second embodiment, the first waveform, which is generated periodically, is compared with the second waveform as a reference to determine the transmission direction of ultrasound waves with the highest similarity. On the other hand, the search unit 111 of the third embodiment performs the search process of the first embodiment as well as that of the second embodiment in parallel. The ultrasound diagnosis apparatus 100 of the third embodiment is similar to that of the second embodiment in other respects. The differences are mainly described below.

To generate the first waveform, the Doppler signal processing unit 108 of the second embodiment generates RAW data of a Doppler spectrum image based on an echo signal in the Doppler mode. In the third embodiment, the Doppler signal processing unit 108 sends the RAW data or the echo signal to the search unit 111. The search unit 111 obtains signal strength in parallel with calculating the similarity of the first waveform. Further, in the third embodiment, the similarity is weighted, and also the signal strength is weighted correspondingly to the weighting of the similarity. Accordingly, the search unit 111 can make an evaluation in association with the level of similarity and the magnitude of signal strength. The search unit 111 makes an evaluation for each transmission direction based on the weight of similarity and that of signal strength. Based on this evaluation, the search unit 111 determines the optimal transmission direction of ultrasound waves, and sends it to the direction setting unit 110.

The ultrasound diagnosis apparatus 100 of the embodiment is configured to search the transmission direction of ultrasound waves based on both the similarity and the signal strength. This improves the accuracy of searching for the transmission direction of ultrasound waves.

[Fourth Embodiment]

In the following, the ultrasound diagnosis apparatus 100 according to the fourth embodiment is described. The ultrasound diagnosis apparatus 100 of the fourth embodiment is different from that of the first and the third embodiment in the start timing of the search process by the search unit 111. The ultrasound diagnosis apparatus 100 of the fourth embodiment is similar to that of the first embodiment in other respects. The differences are mainly described below.

In the first embodiment, the search unit 111 performs the search process at predetermined time intervals. On the other hand, the search unit 111 of the ultrasound diagnosis apparatus 100 of the fourth embodiment continuously or intermittently obtains signal strength in predetermined transmission direction of ultrasound waves. Hereinafter, the operation of the search unit 111 that continuously or intermittently obtains signal strength in predetermined transmission direction of ultrasound waves is sometimes described as "monitoring signal strength" or simply as "monitoring". Besides, the search unit 111 starts the search process when signal strength obtained by monitoring drops below a threshold stored in advance.

<Operation>

Figure 16:
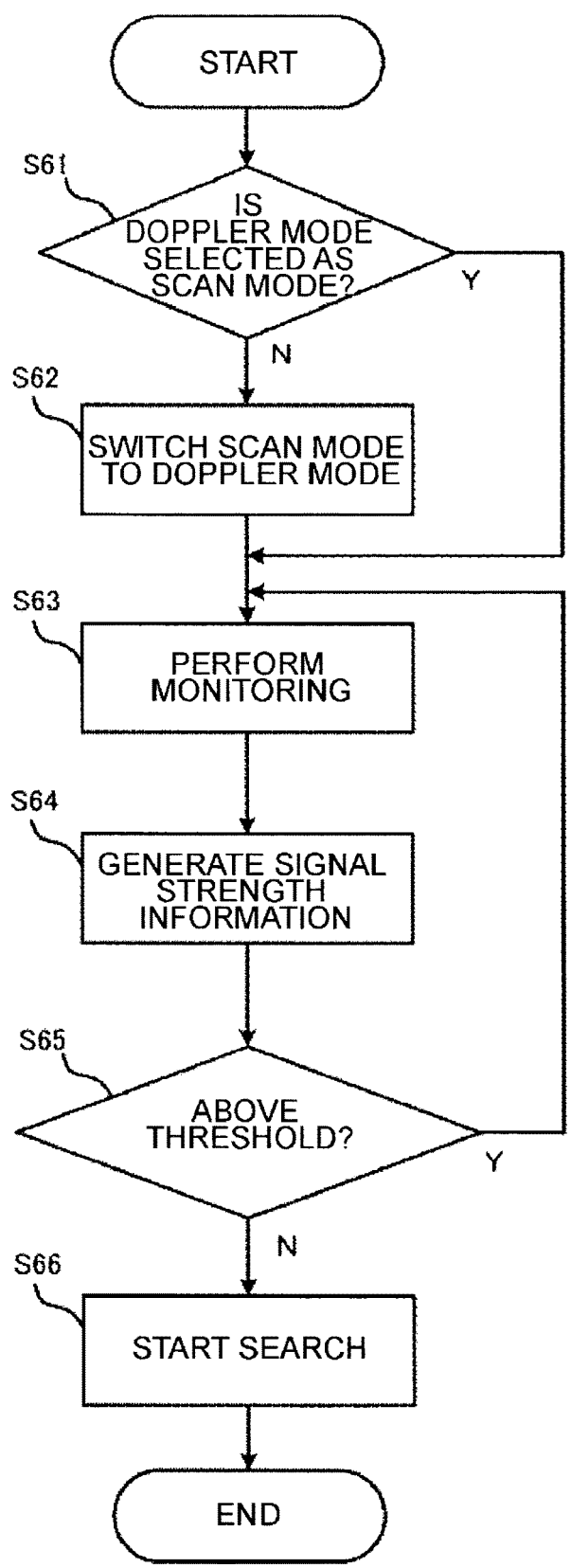
FIG. 16 is a flowchart schematically illustrating the operation of an ultrasound diagnosis apparatus according to a fourth embodiment.

Next, a description is given of a control flow to perform the search process by monitoring signal strength according to the embodiment with reference to FIG. 16. FIG. 16 is a flowchart schematically illustrating the operation of the ultrasound diagnosis apparatus 100 of the fourth embodiment. The steps, in which the operator determines the initial setting including scan mode, and ultrasound waves are transmitted in the selected scan mode, are the same as in the first embodiment, and not described here.

(Step S61)

The main control unit 104 determines whether the Doppler mode is selected as scan mode in the initial setting.

(Step S62)

In step S61, if it is determined that the scan mode is not the Doppler mode (step S61; No), the main control unit 104 switches the scan mode to the Doppler mode to start the monitoring.

(Step S63)

When the scan mode is switched to the Doppler mode in step S62 or if it is determined that the Doppler mode is selected as scan mode in the initial setting at step S61 (step S61; Yes), the monitoring is initiated. The main control unit 104 makes the end part 10 start transmitting ultrasound waves in the Doppler mode via the transmitter unit 105 for the monitoring. If a scan mode other than the Doppler mode (B-mode, etc.) is selected in the initial setting, after the Doppler mode transmission, the scan mode is switched alternately between the Doppler mode and the scan mode selected in the initial setting.

(Step S64)

The receiver unit 106 receives an echo signal based on the Doppler mode from the end part 10. The Doppler signal processing unit 108 performs the signal processing on the echo signal and sends a Doppler signal obtained thereby to the search unit 111. The search unit 111 generates signal strength information based on the Doppler signal in the time corresponding to predetermined cardiac time phase.

(Step S65)

The signal strength information generated as above is compared to a threshold stored in advance. If the signal strength information indicates strength above the threshold (step S65; Yes), steps S63 to S65 are repeated.

(Step S66)

If the search unit 111 determines in step S65 that the signal strength is below the threshold (step S65; No), the main control unit 104 makes the end part 10 start transmitting/receiving ultrasound waves via the transmitter unit 105 for the search process.

The steps of the search process for determining the transmission direction of ultrasound waves and updating the setting of the transmission direction are performed in the same manner as described in the first and the third embodiments. After that, the main control unit 104 repeats steps S63 to S65.

The ultrasound diagnosis apparatus 100 of this embodiment monitors signal strength in a particular direction upon start of transmitting/receiving ultrasound waves in selected scan mode. If the signal strength drops below a threshold, the search unit 111 starts the search process. In the search process, the search unit 111 compares pieces of information on the signal strength of a plurality of Doppler signals corresponding to different transmission directions, thereby determining the transmission direction of ultrasound waves with the highest signal strength. The direction setting unit 110 changes the transmission direction of ultrasound waves at the end part 10 to the transmission direction. Thus, even if the end part 10 shifts in the subject's body due to the breathing, beats, body movement, throat reflection, emetic response, and the like of the subject, and the transmission direction of ultrasound waves shifts from the object to be observed, the ultrasound diagnosis apparatus 100 can change the transmission direction of ultrasound waves to follow the shift, thereby enabling the continuation of monitoring inside the subject' body without imposing burdensome tasks on the operator. Moreover, even in long-term monitoring, the ultrasound diagnosis apparatus 100 can avoid a decrease in the operation efficiency.

As in the first embodiment, the ultrasound diagnosis apparatus 100 of the fourth embodiment may have the end part 10 in a capsule form. Moreover, the end part 10 may have a structure in which only minimal lines such as a signal line and a power supply line are passed through the cable 11. This makes it possible to reduce the burden on the subject compared to the case of using the TEE probe.

Further, in the fourth embodiment, the search unit 111 performs the search process as needed. With this, the ultrasound diagnosis apparatus 100 can correct the transmission direction of ultrasound waves at appropriate timing. In this manner, the ultrasound diagnosis apparatus 100 is further capable of preventing a shift between the observation object and the transmission direction of ultrasound waves. Furthermore, the ultrasound diagnosis apparatus 100 can reduce unnecessary transmission/reception of ultrasound waves.

[Fifth Embodiment]

In the following, the ultrasound diagnosis apparatus 100 according to the fifth embodiment is described. The ultrasound diagnosis apparatus 100 of the fifth embodiment is different from that of the second and the third embodiment in the start timing of the search process by the search unit 111. The ultrasound diagnosis apparatus 100 of the fifth embodiment is similar to that of the second embodiment in other respects. The differences are mainly described below.

In the second embodiment, the search unit 111 performs the search process at predetermined time intervals. On the other hand, the search unit 111 of the ultrasound diagnosis apparatus 100 of the fifth embodiment continuously or intermittently generates a waveform based on a Doppler signal in predetermined transmission direction of ultrasound waves (hereinafter, sometimes referred to as "third waveform"). The third waveform corresponds to an example of "third waveform pattern". The search unit 111 obtains the similarity of the third waveform to the second waveform stored in advance. Hereinafter, the operation of the search unit 111 that continuously or intermittently obtains similarity in predetermined transmission direction of ultrasound waves is sometimes described as "monitoring similarity" or simply as "monitoring". Besides, the search unit 111 starts the search process when similarity obtained by monitoring drops below a threshold stored in advance.

<Operation>

Figure 17:
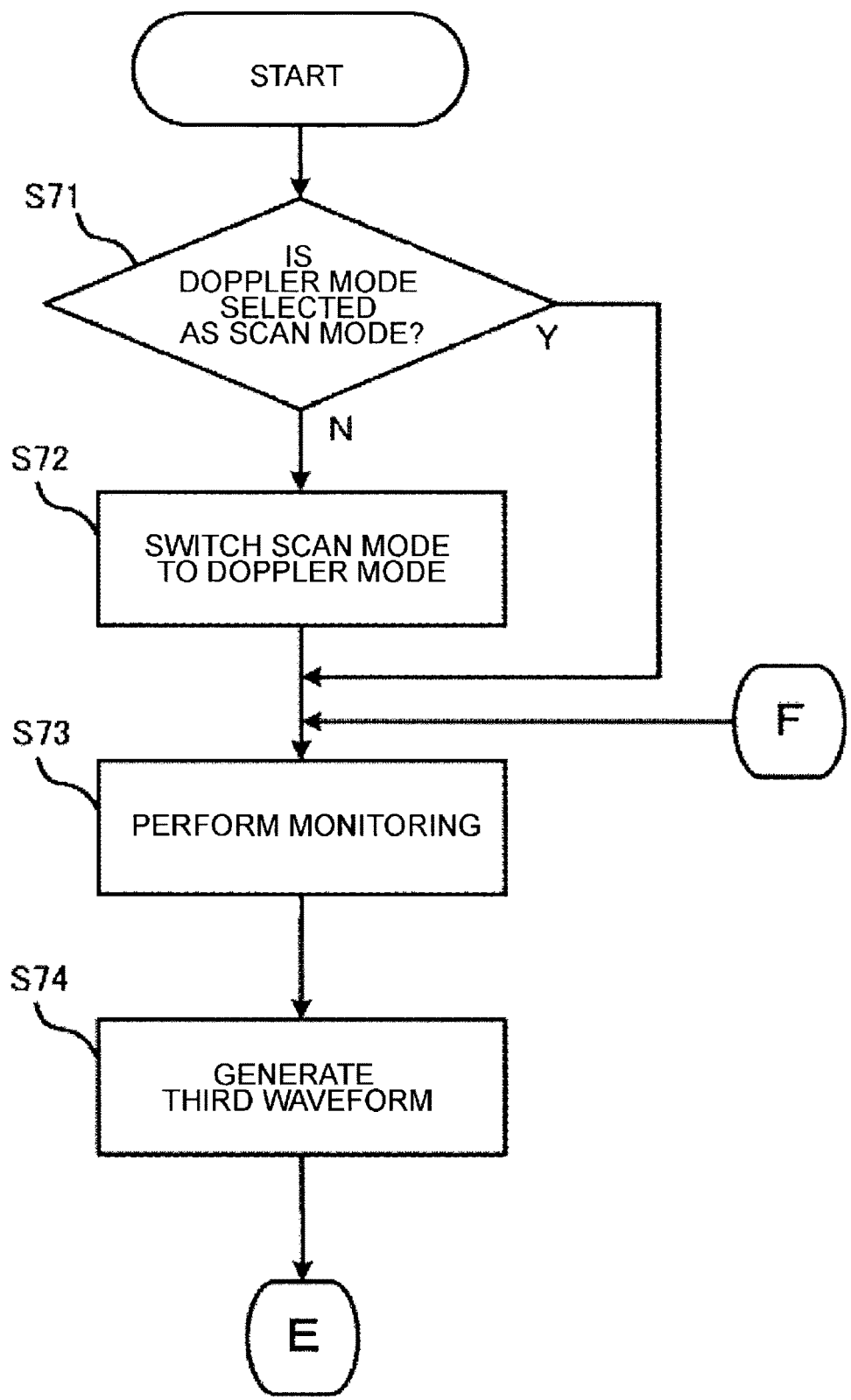
FIG. 17 is a flowchart schematically illustrating the operation of an ultrasound diagnosis apparatus according to a fifth embodiment.
Figure 18:
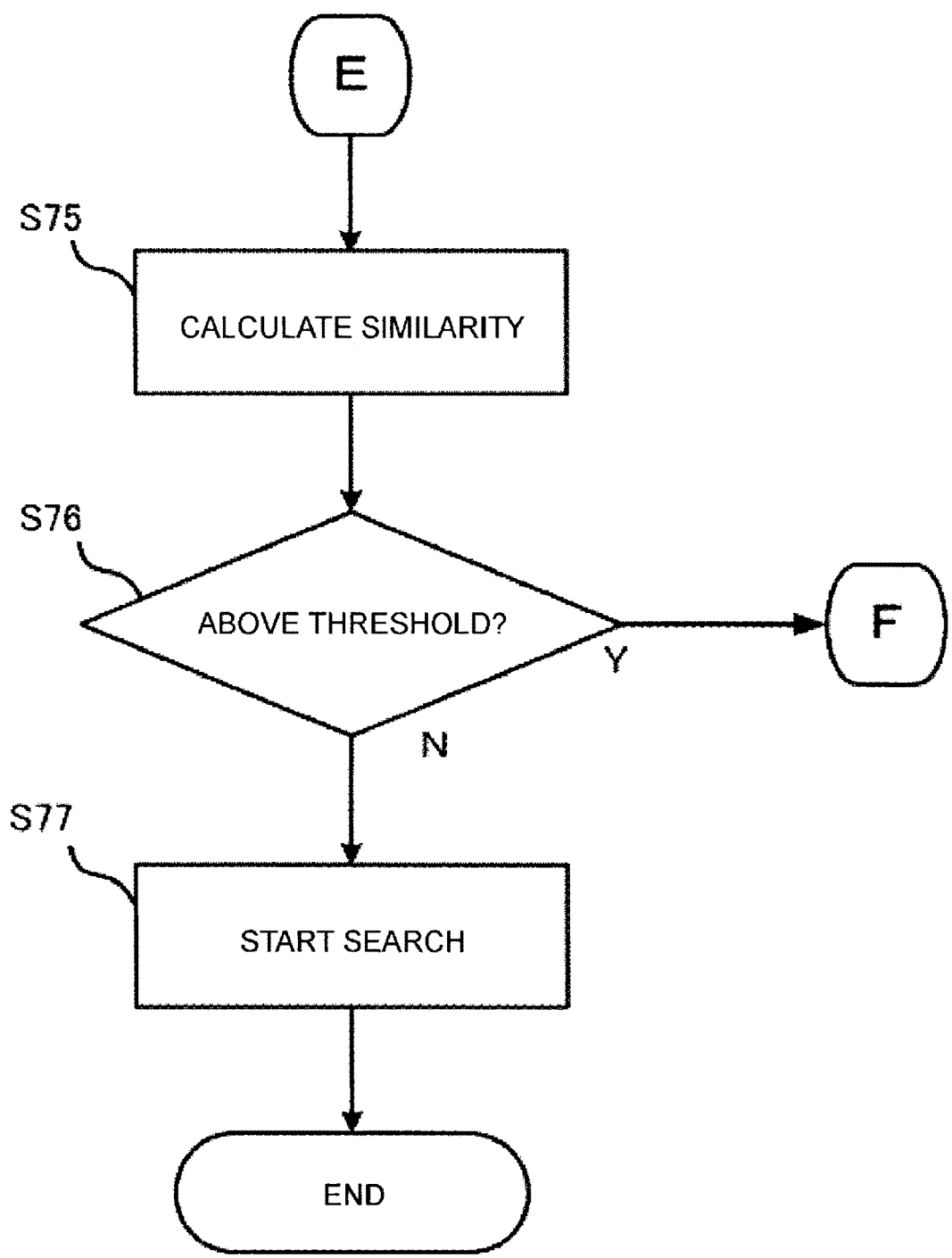
FIG. 18 is a flowchart schematically illustrating the operation of the ultrasound diagnosis apparatus of the fifth embodiment.

Next, a description is given of a control flow to perform the search process by monitoring similarity according to the embodiment with reference to FIG. 17. FIG. 17 is a flowchart schematically illustrating the operation of the ultrasound diagnosis apparatus 100 of the fifth embodiment. The steps, in which the operator determines the initial setting including scan mode, and ultrasound waves are transmitted in the selected scan mode, are the same as in the second embodiment, and not described here.

(Step S71)

The main control unit 104 determines whether the Doppler mode is selected as scan mode in the initial setting.

(Step S72)

In step S71, if it is determined that the scan mode is not the Doppler mode (step S71; No), the main control unit 104 switches the scan mode to the Doppler mode to start the monitoring.

(Step S73)

When the scan mode is switched to the Doppler mode in step S72 or if it is determined that the Doppler mode is selected as scan mode as the initial setting in step S71 (step S71; Yes), the monitoring is initiated. The main control unit 104 makes the end part 10 start transmitting ultrasound waves in the Doppler mode via the transmitter unit 105 for the monitoring. If a scan mode other than the Doppler mode (B-mode, etc.) is selected in the initial setting, after the Doppler mode transmission, the scan mode is switched alternately between the Doppler mode and the scan mode selected in the initial setting.

(Step S74)

The receiver unit 106 receives an echo signal based on the Doppler mode from the end part 10. The Doppler signal processing unit 108 performs the signal processing on the echo signal and sends RAW data obtained thereby to the generating unit 109. The generating unit 109 generates a Doppler spectrum image based on the RAW data. The search unit 111 generates the third waveform from the Doppler spectrum image generated by the generating unit 109 in the monitoring.

(Step S75)

The search unit 111 calculates the similarity of the third waveform to the second waveform stored in advance.

(Step S76)

The similarity obtained as above is compared to a threshold stored in advance. If the third waveform indicates similarity above the threshold (step S76; Yes), steps S73 to S76 are repeated.

(Step S77)

If the search unit 111 determines in step S76 that the similarity is below the threshold (step S76; No), the main control unit 104 makes the end part 10 start transmitting/receiving ultrasound waves via the transmitter unit 105 for the search process.

The steps of the search process for determining the transmission direction of ultrasound waves and updating the setting of the transmission direction are performed in the same manner as described in the second and the third embodiment. After that, the main control unit 104 repeats steps S73 to S77.

The ultrasound diagnosis apparatus 100 of this embodiment monitors similarity between the third waveform and the second waveform in a particular direction upon start of transmitting/receiving ultrasound waves in selected scan mode. If the similarity drops below a threshold, the search unit 111 starts the search process. In the search process, the search unit 111 obtains similarity between each of a plurality of first waveforms corresponding to different transmission directions and the second waveform, thereby determining the transmission direction of ultrasound waves corresponding to the first waveform with the highest similarity among obtained similarities. The direction setting unit 110 changes the transmission direction of ultrasound waves at the end part 10 to the transmission direction. Thus, even if the end part 10 shifts in the subject's body due to the breathing, beats, body movement, throat reflection, emetic response, and the like of the subject, and the transmission direction of ultrasound waves shifts from the object to be observed, the ultrasound diagnosis apparatus 100 can change the transmission direction of ultrasound waves to follow the shift, thereby enabling the continuation of monitoring inside the subject' body without imposing burdensome tasks on the operator. Moreover, even in long-term monitoring, the ultrasound diagnosis apparatus 100 can avoid a decrease in the operation efficiency.

As in the first embodiment, the ultrasound diagnosis apparatus 100 of the fifth embodiment may have the end part 10 in a capsule form. Moreover, the end part 10 may have a structure in which only minimal lines such as a signal line and a power supply line are passed through the cable 11. This makes it possible to reduce the burden on the subject compared to the case of using the TEE probe.

Further, in the fifth embodiment, the search unit 111 performs the search process as needed. With this, the ultrasound diagnosis apparatus 100 can correct the transmission direction of ultrasound waves at appropriate timing. In this manner, the ultrasound diagnosis apparatus 100 is further capable of preventing a shift between the observation object and the transmission direction of ultrasound waves. Furthermore, the ultrasound diagnosis apparatus 100 can reduce unnecessary transmission/reception of ultrasound waves.

[Sixth Embodiment]

In the following, the ultrasound diagnosis apparatus 100 according to the sixth embodiment is described. In the fifth embodiment, similarity is monitored between the third waveform and the second waveform in a particular direction. When the similarity drops below a threshold, the search process starts. On the other hand, the search unit 111 of the fifth embodiment performs the monitoring of the fourth embodiment as well as that of the fifth embodiment in parallel. The ultrasound diagnosis apparatus 100 of the sixth embodiment is similar to that of the fifth embodiment in other respects. The differences are mainly described below.

In the fifth embodiment, the search unit 111 monitors similarity between the third waveform and the second waveform in a predetermined direction upon start of transmitting/receiving ultrasound waves in selected scan mode. On the other hand, in the sixth embodiment, the search unit 111 monitors signal strength of a Doppler signal in the predetermined direction in parallel with monitoring similarity between the third waveform and the second waveform. The "predetermined direction" as used herein is the same direction as the transmission direction of ultrasound waves in the third waveforms. The search unit 111 of the sixth embodiment starts the search process when each or both of similarity and signal strength drop below their thresholds, respectively. The search process may be the same as that of any one of the first to the third embodiments.

The ultrasound diagnosis apparatus 100 of the embodiment is configured to determine the timing of starting the search process by monitoring similarity and signal strength. With this, the ultrasound diagnosis apparatus 100 can correct the transmission direction of ultrasound waves at appropriate timing. In this manner, the ultrasound diagnosis apparatus 100 is further capable of preventing a shift between the observation object and the transmission direction of ultrasound waves. Furthermore, the ultrasound diagnosis apparatus 100 can reduce unnecessary transmission/reception of ultrasound waves.

[Seventh Embodiment]

In the following, the seventh embodiment is described. The search unit 111 of the first to the sixth embodiments is configured to search for the optimal transmission direction of ultrasound wave through any one of the search processes as described above. The seventh embodiment is the same in this respect. However, the search unit of the seventh embodiment further performs, when there is found no suitable transmission direction of ultrasound waves, error notification, termination of ultrasound monitoring (transmitting/receiving ultrasound waves), and the like. The ultrasound diagnosis apparatus 100 of the embodiment is similar to that of the first to sixth embodiments in other aspects. The differences are mainly described below.

(Search Process—Signal Strength)

The search unit 111 of the seventh embodiment stores a threshold for signal strength. In the search process, having determined the highest signal strength, the search unit 111 compares the signal strength with the threshold. If the signal strength is below the threshold, the search unit 111 determines that there is found no suitable transmission direction of ultrasound waves. Then, the search unit 111 notifies, via a notification unit (not illustrated), the operator of recognizable error information. For example, the notification unit displays an error message on the display unit 103. For another example, the notification unit outputs predetermined sound from an audio output unit (not illustrated). In this case, the search unit 111 does not send information on the transmission direction of ultrasound waves to the direction setting unit 110.

As another operation of the search unit 111, if the signal strength is below the threshold, the search unit 111 determines that there is found no suitable transmission direction of ultrasound waves. Then, the search unit 111 informs the main control unit 104 of this. Upon receipt of the information, the main control unit 104 stops the transmission of ultrasound waves by the end part 10. As an example of the situation where the search unit 111 cannot find the suitable transmission direction of ultrasound waves may be cited a case where the shift of the end part 10 is large. In this case, the observation object is likely to be not included in ROI even if the direction setting unit 110 rotates/tilts the ultrasound transducer 12 and changes the transmission direction of ultrasound waves by electronic scanning.

(Search Process—Similarity)

The search unit 111 of the seventh embodiment stores a threshold for similarity. In the search process, having determined the transmission direction of ultrasound waves with the highest similarity, the search unit 111 compares the similarity with the threshold. If the similarity is below the threshold, the search unit 111 determines that there is found no suitable transmission direction of ultrasound waves. Then, the search unit 111 notifies, via the notification unit (not illustrated), the operator of recognizable error information. The notification unit operates in the same manner as described above. Also, the main control unit 104 stops the transmission of ultrasound waves by the end part 10 in the same manner as described above.

As in the third embodiment, when both signal strength and similarity are used in the search process, the search unit 111 performs a combination of the above processes.

In this embodiment, the search unit 111 is configured to perform, when there is found no optimal transmission direction of ultrasound waves, error notification, termination of ultrasound transmission, and the like. For example, if the observation object is not included in ROI even by rotating/tilting the ultrasound transducer 12 and changing the transmission direction of ultrasound waves in electronic scanning, the operator needs to recognize the situation. In addition, the end part 10 is required to be removed in such a situation. In this respect, according to the embodiment, when the end part 10 has shifted largely with respect to the subject, the operator can handle the situation appropriately.

[Usage Example]

Described below is an example of how to use the ultrasound diagnosis apparatus 100 according to the first to the seventh embodiments. An example is described in which the ultrasound diagnosis apparatus 100 is used to monitor cardiac ejection fraction.

(Display B-Mode Image)

For monitoring cardiac ejection fraction, the ultrasound diagnosis apparatus 100 displays a B-mode image of the heart on the display unit 103. This is conducted, for example, as follows. First, the operator determines the initial setting, in which the B-mode is selected as scan mode, using the operation unit 102. According to the initial setting, the transmitter unit 105 sends the end part 10 a drive control signal of the ultrasound transducer 12 in the B-mode. The ultrasound transducer 12 is driven by the transmitter 141 of the end part 10, and ultrasound waves are transmitted to the subject.

Through the receiver 142 or the like, the end part 10 sends echo signals to the main body 101. Through the receiver unit 106 or the like, the main body 101 sends the echo signals to the B-mode signal processing unit 107. The B-mode signal processing unit 107 performs the signal processing on the echo signals, thereby generating RAW data related to the echo signals in the B-mode. Having received the RAW data from the B-mode signal processing unit 107, the generating unit 109 generates B-mode image data. The generating unit 109 displays a B-mode image on the display unit 103 based on the B-mode image data. Then, the end part 10 is inserted into the subject's body by the operator. Referring to the B-mode image, the operator inserts the end part 10 into the subject's body.

(Set Contour)

The operator inserts the end part 10 in the subject's body to a predetermined position in the esophagus. Then, the operator adjusts the position of the ultrasound transducer 12 (rotate, tilt, etc.) or adjusts the ultrasound beam angle, so that the heart is included in ROI. With this, the display unit 103 displays a B-mode image representing a cross section of the heart. In the B-mode image of the heart, the main control unit 104 sets a contour at the boundary between the myocardium and the heart chamber (hereinafter, referred to as "myocardium/heart chamber boundary"). For example, the main control unit 104 extracts a contour corresponding to the boundary position in the cardiac cavity by manual setting of the operator, or by using an automatic method such as ACT (Automated-Contour-Tracking). This contour is used when the heart chamber volume is obtained for calculating the cardiac ejection fraction through, for example, modified Simpson's method, Area-Length method, or the like.

Figure 19:
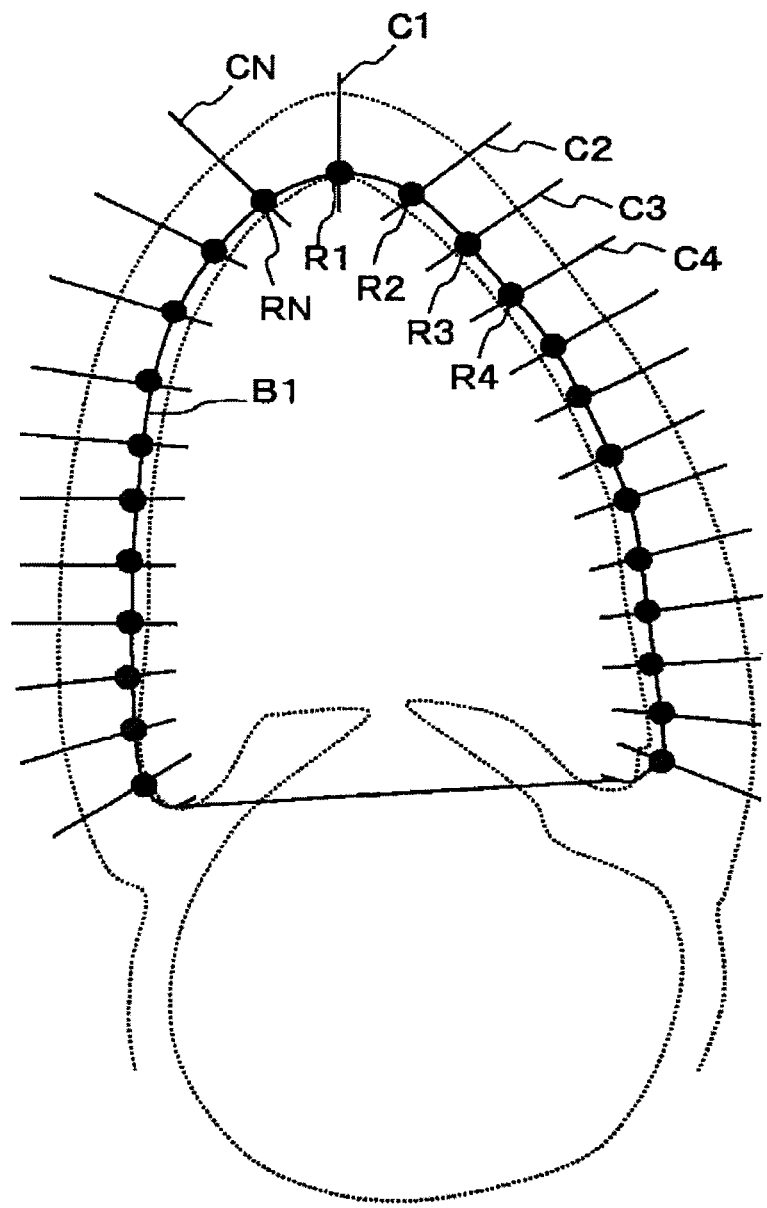
FIG. 19 is a schematic diagram illustrating a contour and operation points set on a B-mode image.

A specific example of the contour setting is described with reference to FIG. 19. FIG. 19 is a schematic diagram illustrating a contour and operation points set on an apical two-chamber view. As illustrated in FIG. 19, the operator sets, through the operation unit 102, a closed curve B1 at a predetermined position in the heart chamber indicated on the B-mode image. As illustrated in FIG. 19, the main control unit 104 sets a plurality of operation points R1, R2, R3, ..., RN on the closed curve at predetermined intervals. The main control unit 104 moves the operation points radially toward the myocardium. For example, the main control unit 104 moves the operation points R1, R2, R3, ..., RN on the closed curve B1 along their normal directions C1, C2, C3, ..., CN, respectively.

While moving the operation points RN, R1, R2, R3, ..., RN radially, the main control unit 104 continuously obtains a pixel value in the B-mode image data corresponding to the position of each of the operation points R1, R2, R3, ..., RN. Then, the main control unit 104 detects a boundary position between the myocardium and the heart chamber where the pixel value changes suddenly. Besides, the main control unit 104 generates contour data by connecting a plurality of boundary positions detected as above. In this generation of the contour data, regarding image data, the main control unit 104 sequentially retrieves pixel values corresponding to the positions of the operation points R1, R2, R3, ..., RN that radially move in the heart chamber, thereby obtaining the amount of change in pixel value. The main control unit 104 detects the boundary between the heart chamber in which reflection of ultrasound waves is small and the myocardium with relatively large reflection (myocardium/heart chamber boundary) based on the change amount.

(Sampling Gate Set)

The operator sets sampling gate to be superimposed on a B-mode image indicating the heart using the operation unit 102. FIG. 6 illustrates the transmission direction of the ultrasound waves in the pulsed Doppler (beam angle from the sound source) without the illustration of the sampling gate. For example, the operator sets the sampling gate to be superimposed on a broken line L1 in FIG. 6. The broken line L1 runs from left atrium LA through mitral valve M to the left chamber in the B-mode image, and passes by the center of the left heart system. For example, the sampling gate is set in an area of the left ventricular cavity around the mitral valve M. This is the direction in which the strength of blood flow is likely to be detected as being large.

(Heart Chamber Volume Measurement)

Figure 20A:
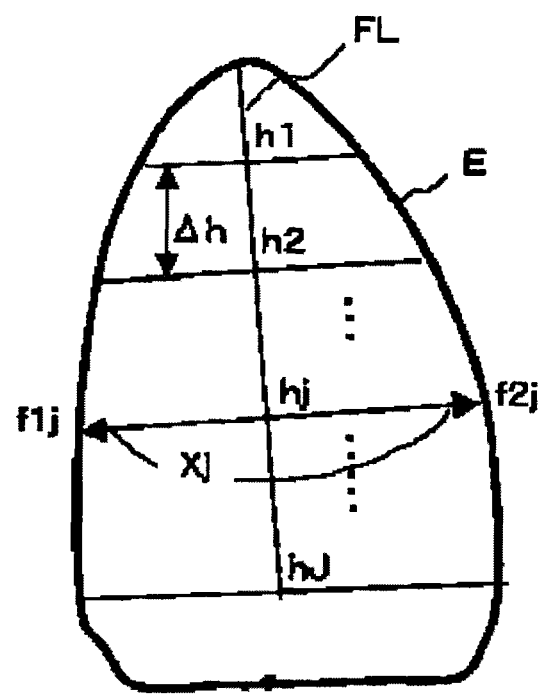
FIG. 20A is a schematic diagram illustrating a specific example of heart chamber volume measurement performed by a main control unit.
Figure 20B:
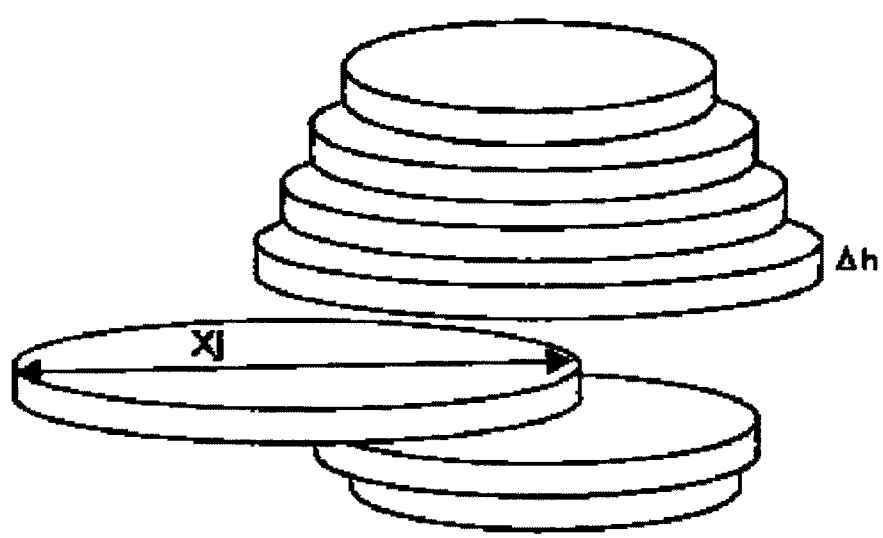
FIG. 20B is a schematic diagram illustrating a specific example of heart chamber volume measurement performed by the main control unit.

FIGS. 20A and 20B illustrate a specific example of the heart chamber volume measurement performed by the main control unit 104. Having received a selection operation through the operation unit 102, the main control unit 104 selects M pieces of image data P1 to PM corresponding to desired time period T0 from time-series B-mode image data stored in the storage unit (not illustrated), and stores them in the storage unit separately. The main control unit 104 also detects the valve annulus from the contour data generated for each of the image data P1 to PM, and sets the longitudinal axis FL of the heart based on the position of the valve annulus. In addition, the main control unit 104 draws normals to the longitudinal axis FL to pass division points hj (j=1 to J) to divide the longitudinal axis FL into J parts at interval $\Delta h$. The main control unit 104 calculates length Xj (j=1 to J) between two intersections f1j and f2j where the normal intersects contour data E (see FIG. 20A).

The main control unit 104 measures the heart chamber volume in each time phase using a method of approximating the volume by the sum of small cylinders with the length X1 to Xj determined in the above manner as the diameter and the interval $\Delta h$ set in advance as the height, i.e., so-called disk summation method (see FIG. 20B). The heart chamber volume measured for each time phase is stored in a memory circuit (not illustrated) of the main control unit 104 with the time phase as incidental information.

(Cardiac Ejection Fraction Measurement)

Further, the main control unit 104 acquires heart chamber volume Vxs at end-systole and heart chamber volume Vxd at end-diastole from the heart chamber volume data stored in the memory circuit thereof. Thus, the main control unit 104 calculates the cardiac ejection fraction Zx based on the following formula (1):

$$Zx=(Vxd-Vxs)/Vxd \times 100 (\%) \quad (1)$$

The measurement of the cardiac ejection fraction as described above is continuously performed until terminated by the operator or set monitoring period has elapsed.

(Monitoring Process)

The main control unit 104 starts the search process at the start timing described in any one of the first to the sixth embodiment. For example, in the ultrasound diagnosis apparatus 100, the search unit 111 sequentially obtains the third waveform in the above direction of FIG. 6. The search unit 111 monitors the similarity between the third waveform and the second waveform. For example, if the end part 10 has shifted relatively with respect to an observation site inside the subject's body due to peristaltic motion, the similarity between the third waveform and the second waveform drops below the threshold in the monitoring of the search unit 111. Thereby, the search process of the ultrasound diagnosis apparatus 100 is started.

(Search Process)

In the search process, based on a control signal received from the transmitter unit 105, the end part 10 transmits ultrasound waves in the transmission direction of ultrasound waves passing through the sampling gate and in peripheral directions adjacent to the transmission direction at a predetermined angle. The search unit 111 obtains similarity between each of a plurality of first waveforms corresponding to different transmission directions and the second waveform, thereby determining the transmission direction of ultrasound waves corresponding to the first waveform with the highest similarity among obtained similarities. The search unit 111 determines whether the highest similarity drops below the threshold. If the suitable transmission direction of ultrasound waves is found, the direction setting unit 110 changes the beam angle of ultrasound waves based on information on the transmission direction. At this time, through the direction controller 16 of the end part 10, the direction setting unit 110 drives the drive unit 18, thereby rotating/tilting the ultrasound transducer 12. Besides, the search unit 111 may compare the similarities of waveforms while the depth of the sampling gate is varied to obtain the depth with the highest similarity, and change the sampling gate to the depth thus obtained.

(Error Handling)

If there is found no suitable transmission direction of ultrasound waves, for example, the search unit 111 displays an error message such as "Transmission Direction Error" on the display unit 103, and also outputs sound indicating error from the audio output unit. If there is found no suitable transmission direction of ultrasound waves, the search unit 111 may send an error signal to the main control unit 104. Upon receipt of the error signal, the main control unit 104 terminates the monitoring by ultrasound waves. Having been notified of the error, the operator can recognize that the end part 10 had shifted, and adjust the position of the end part 10 manually by the cable 11. Further, the operator can operate the ultrasound wave radiation surface so that the heart is included in ROI by driving the drive unit 18 using the operation unit 102 to rotate/tilt the ultrasound transducer 12.

As well as cardiac ejection fraction, the ultrasound diagnosis apparatus 100 can monitor heart chamber volume (including left ventricular volume, left atrial volume, etc.), mitral regurgitation, and left ventricular inflow in the vicinity of the mitral valve. Also, in view of such a situation that the operator notices an obvious position shift while viewing an ultrasound image, the ultrasound diagnosis apparatus 100 may be configured so that the search process can be performed immediately through the operation unit 102.

With the ultrasound diagnosis apparatus 100 according to the first to seventh embodiments described above, even if the end part 10 shifts in the subject's body due to the breathing, beats, body movement, throat reflection, emetic response, and the like of the subject, and the transmission direction of ultrasound waves shifts from the object to be observed, it is possible to change the transmission direction of ultrasound waves to follow the shift, thereby enabling the continuation of monitoring inside the subject' body without imposing burdensome tasks on the operator. Moreover, even in long-term monitoring, the ultrasound diagnosis apparatus 100 can avoid a decrease in the operation efficiency.

The first to the seventh embodiments can be used in any combination as appropriate. In the embodiments, not only the end part 10 in a capsule form, but a TEE probe may also be used in the configuration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
   an ultrasound transceiver configured to
   change a transmission direction of ultrasound waves, and
   transmit the ultrasound waves continuously or repeatedly at predetermined intervals, the ultrasound waves being transmitted in a direction set while the ultrasound transceiver is inserted and placed in an esophagus of a subject to acquire biological information including a Doppler signal indicating blood flow information of an observation site of the subject, the observation site being heart of the subject; and
   a controller configured to
   obtain a direction toward the observation site based on a signal strength of the Doppler signal or a measured waveform pattern of the Doppler signal, and
   control, based on the obtained direction, the ultrasound transceiver being inserted and placed in the esophagus to adjust the transmission direction of ultrasound waves to be the obtained direction.

2. The ultrasound diagnosis apparatus according to claim 1, further comprising a display unit configured to display the condition of the observation site based on the biological information.

3. The ultrasound diagnosis apparatus according to claim 1, wherein
   the controller is configured to control the ultrasound transceiver to sequentially change the transmission direction of ultrasound waves, and obtain a transmission direction in which signal strength of the Doppler signal is highest as the direction toward the observation site.

4. The ultrasound diagnosis apparatus according to claim 3, wherein the controller is configured to obtain the transmission direction in which the signal strength of the Doppler signal is highest as the direction toward the observation site at predetermined time intervals.

5. The ultrasound diagnosis apparatus according to claim 3, wherein the controller is configured to obtain the transmission direction in which the signal strength of the Doppler signal is highest as the direction toward the observation site when the signal strength of the Doppler signal obtained by the ultrasound transceiver is below a threshold stored in advance.

6. The ultrasound diagnosis apparatus according to claim 1, further comprising processing circuitry configured to generate first waveform patterns based on Doppler signals indicating blood flow information of the subject obtained by the ultrasound transceiver as the biological information, wherein
the controller is configured to control the ultrasound transceiver to change the transmission direction of ultrasound waves, and, from the first waveform patterns each generated for a transmission direction, obtain a similar waveform pattern which is most similar to a second waveform pattern stored in advance, and obtain the transmission direction for which the similar waveform pattern is generated as the direction toward the observation site.

7. The ultrasound diagnosis apparatus according to claim 6, wherein the controller is configured to obtain the similar waveform pattern at predetermined time intervals.

8. The ultrasound diagnosis apparatus according to claim 6, wherein
the processing circuitry is configured to generate a third waveform pattern based on a Doppler signal in a predetermined transmission direction, and
the controller is configured to obtain similarity between the third waveform pattern and the second waveform pattern, and start a process to obtain the similar waveform pattern when the similarity is below a threshold stored in advance.

9. The ultrasound diagnosis apparatus according to claim 3, wherein
the direction in which the ultrasound transceiver transmits ultrasound waves is set to direction of left ventricle of the subject, and
the ultrasound transceiver is configured to obtain a Doppler signal from the left ventricle as the biological information.

10. The ultrasound diagnosis apparatus according to claim 2, wherein the controller is configured to sequentially receive an electrocardiogram waveform of the subject and obtain predetermined cardiac time phase, and control the ultrasound transceiver to transmit ultrasound waves to obtain the Doppler signal based on the cardiac time phase.

11. The ultrasound diagnosis apparatus according to claim 10, wherein the predetermined cardiac time phase is diastole.

12. The ultrasound diagnosis apparatus according to claim 3, wherein
the ultrasound transceiver is configured to be included in a capsule container, and
the capsule container further includes an interface configured to transmit and receive signals between the capsule container and a main body, and a power supply line configured to supply power to the ultrasound transceiver.

13. The ultrasound diagnosis apparatus according to claim 6, wherein the second waveform pattern is generated based on the biological information acquired under a predetermined acquisition condition determined in advance, and stored.

14. The ultrasound diagnosis apparatus according to claim 2, wherein
the biological information includes a Doppler signal indicating blood flow information of the subject, and
the controller is configured to obtain a position of the observation site based on the Doppler signal sequentially obtained.

15. The ultrasound diagnosis apparatus according to claim 1, wherein the biological information includes at least one of heart chamber volume, cardiac ejection fraction, and blood flow information of the observation site.

16. The ultrasound diagnosis apparatus according to claim 12, wherein
the main body includes:
a power supply connected to the power supply line; and
a signal processor connected to the controller and the interface, and configured to perform signal processing on signals received from the ultrasound transceiver, and
the capsule container is configured to be connected to the main body by the interface.

17. The ultrasound diagnosis apparatus according to claim 6, wherein
the ultrasound transceiver is configured to be included in a capsule container, and
the capsule container further includes an interface configured to transmit and receive signals between the capsule container and a main body, and a power supply line configured to supply power to the ultrasound transceiver.

18. An ultrasound diagnosis apparatus, comprising:
an ultrasound transceiver configured to update a transmission direction of ultrasound waves to follow an observation site inside of a subject, thereby correcting the transmission direction to compensate for a shift of a position of the ultrasound transceiver shifts relative to a position of the observation site, the ultrasound transceiver performing the update of the transmission direction by
transmitting the ultrasound waves in the transmission direction of the observation site, the ultrasound waves being transmitted continuously or repeatedly at predetermined intervals, and
changing the transmission direction of the ultrasound waves while the ultrasound transceiver is inserted and placed in an esophagus of the subject to acquire biological information including a Doppler signal indicating blood flow information of the observation site inside of the subject, the observation site being heart of the subject; and
a controller configured to
determine, based on either (i) a signal strength of the Doppler signal or (ii) a waveform pattern of the Doppler signal, a direction from ultrasound transceiver to the observation site, and
control the ultrasound transceiver that is inserted and placed in the esophagus to update the transmission direction to the determined direction from ultrasound transceiver to the observation site.

* * * * *